US012145988B2

(12) United States Patent
Holtzman et al.

(10) Patent No.: US 12,145,988 B2
(45) Date of Patent: Nov. 19, 2024

(54) ANTI-TREM-2 AGONIST ANTIBODIES

(71) Applicant: Washington University, St. Louis, MO (US)

(72) Inventors: David Holtzman, St. Louis, MO (US); Jason Ulrich, St. Louis, MO (US); Hong Jiang, St. Louis, MO (US)

(73) Assignee: Washington University, St. Louis, MO (US)

( * ) Notice: Subject to any disclaimer, the term of this patent is extended or adjusted under 35 U.S.C. 154(b) by 892 days.

(21) Appl. No.: 17/275,092

(22) PCT Filed: Sep. 11, 2019

(86) PCT No.: PCT/US2019/050575
§ 371 (c)(1),
(2) Date: Mar. 10, 2021

(87) PCT Pub. No.: WO2020/055975
PCT Pub. Date: Mar. 19, 2020

(65) Prior Publication Data
US 2021/0284727 A1 Sep. 16, 2021

Related U.S. Application Data

(60) Provisional application No. 62/729,458, filed on Sep. 11, 2018.

(51) Int. Cl.
*C07K 16/28* (2006.01)
(52) U.S. Cl.
CPC .... *C07K 16/2803* (2013.01); *C07K 2317/565* (2013.01); *C07K 2317/567* (2013.01); *C07K 2317/75* (2013.01)
(58) Field of Classification Search
CPC .......... C07K 16/2803; C07K 2317/565; C07K 2317/567; C07K 2317/75
See application file for complete search history.

(56) References Cited

U.S. PATENT DOCUMENTS

| 4,741,900 | A | 5/1988 | Alvarez et al. |
| 2014/0370619 | A1 | 12/2014 | Holtzman et al. |
| 2015/0140672 | A1 | 5/2015 | Bateman et al. |
| 2015/0254421 | A1 | 9/2015 | Bateman et al. |
| 2017/0240631 | A1 | 8/2017 | Monroe et al. |
| 2018/0155414 | A1 | 6/2018 | Butovsky et al. |

FOREIGN PATENT DOCUMENTS

| WO | WO-2015116753 A1 * | 8/2015 | ............. A61K 38/08 |
| WO | 2017058866 A1 | 4/2017 | |
| WO | WO-2017062672 A2 * | 4/2017 | ................ A61P 1/04 |
| WO | 2018015573 A2 | 1/2018 | |
| WO | 2020055975 A1 | 3/2020 | |

OTHER PUBLICATIONS

Morris et al., Questions concerning the role of amyloid-β in the definition, aetiology and diagnosis of Alzheimer's disease, 2018, Acta Neuropathologica, vol. 136, pp. 663-689 (Year: 2018).*
Mullane et al., Alzheimer's disease (AD) therapeutics—1: Repeated clinical failures continue to question the amyloid hypothesis of AD and the current understanding of AD causality, 2018, Biochemical Pharmacology, vol. 158, pp. 359-375 (Year: 2018).*
Mayo Clinic, Alzheimer's Disease, 2015, retrieved from: http://www.mayoclinic.org/diseases-conditions/alzheimers-disease/basics/causes/con-20023871 (Year: 2015).*
Ma, Animal Models of Disease, 2004, Modern Drug Discovery, pp. 30-36 (Year: 2004).*
Richardson et al., Mouse Models of Alzheimer's Disease: A Quest for Plaques and Tangles, 2002, ILAR Journal, vol. 43, No. 2, pp. 89-99 (Year: 2002).*
Gotz et al., Rodent models for Alzheimer disease, 2018, Nature Reviews, vol. 19, pp. 583-598 (Year: 2018).*
Sela-Culang et al., The structural basis of antibody-antigen recognition, 2013, Frontiers in Immunology, vol. 4, Article 302, pp. 1-13 (Year: 2013).*
Kussie et al., A Single Engineered Amino Acid Substitution Changes Antibody Fine Specificity, 1994, Journal of Immunology, pp. 146-152 (Year: 1994).*
Chen et al., Enhancement and destruction of antibody function by somatic mutation: unequal occurrence is controlled by the V gene combinatorial associations, 1995, The EMBO Journal, vol. 14, No. 12, pp. 2784-2794 (Year: 1995).*
Albert, M. et al., "The diagnosis of mild cognitive impairment due to Alzheimer's disease: Recommendations from the National Institute on Aging-Alzheimer's Association workgroups on diagnostic guidelines for Alzheimer's disease," Alzheimer's & Dementia, 2011, pp. 270-279, vol. 7, No. 3.
Almagro, J. et al., "Humanization of antibodies," Front. Biosci., Jan. 1, 2008, pp. 1619-1633, vol. 13, No. 5.
Chothia, C. et al., "Canonical Structures for the Hypervariable Regions of Immunoglobulins," J. Mol. Biol., 1987, pp. 901-917, vol. 196.
Fagan, A, et al., "Inverse Relation between in Vivo Amyloid Imaging Load and Cerebrospinal Fluid Alphabeta42 in Humans," Ann. Neurol., 2006, pp. 512-519, vol. 59, No. 3.
International Search Report and Written Opinion dated Dec. 23, 2019 from related PCT Application No. PCT/US/2019/050575; 8 pgs.
Klunk, W. et al., "Imaging Brain Amyloid in Alzheimer's Disease with Pittsburgh Compound-B," Ann. Neurol., 2004, pp. 306-319, vol. 55, No. 3.
Lefranc, M-P., "Definition of the FR-IMGT and CDR-IMGT regions," IMGT Scientific Chart available online at: www.mgt.org/IMGTScientificChart/Nomenclature/IMGT-FRCDRdefinition.html, Mar. 25, 1997, 2 pgs.
Lefranc, M-P et al., "IMGT, the international ImMunoGeneTics information system," Nucleic Acids Res., 2009, pp. D1006-D1012, vol. 37, Database issue.

(Continued)

Primary Examiner — Jeffrey Stucker
Assistant Examiner — Brittney E Donoghue
(74) Attorney, Agent, or Firm — Polsinelli PC

(57) ABSTRACT

The present disclosure encompasses anti-TREM-2 antibodies that promote TREM-2 activation and methods of using the anti-TREM-2 agonist antibodies therapeutically.

9 Claims, 1 Drawing Sheet
Specification includes a Sequence Listing.

(56) References Cited

OTHER PUBLICATIONS

Maccallum, R. et al., "Antibody-antigen Interactions: Contact Analysis and Binding Site Topography," J. Mol. Biol., Oct. 11, 1996, pp. 732-745, vol. 262, No. 5.
Mckhann, G. et al., "The diagnosis of dementia due to Alzheimer's disease: Recommendations from the National Institute on Aging-Alzheimer's Association workgroups on diagnostic guidelines for Alzheimer's disease," Alzheimer's & Dementia, May 2011, pp. 263-269, vol. 7, No. 3.
Sperling, R. et al., "Toward defining the preclinical stages of Alzheimer's disease: Recommendations from the National Institute on Aging-Alzheimer's Association workgroups on diagnostic guidelines for Alzheimer's disease," Alzheimer's & Dementia, May 2011, pp. 280-292, vol. 7, No. 3.
Clackson, T. et al., "Making antibody fragments using phage display libraries," Nature, Aug. 15, 1991, pp. 624-628, vol. 352.
Lefranc, M-P., "The IMGT Unique Numbering for Immunoglobulins, T-Cell Receptors, and Ig-Like Domains," The Immunologist, 1999, pp. 132-136, vol. 7, No. 4.
Portolano, S. et al., "Lack of Promiscuity in Autoantigen-Specific H and L Chain Combinations as Revealed by Human H and L Chain 'Routlette'," J. Immunol., Feb. 1, 1993, pp. 880-887, vol. 150, No. 3.
Cheng Q., et al., "TREM2-Activating Antibodies Abrogate the Negative Pleiotropic Effects of the Alzheimer's Disease Variant Trem2R47H on Murine Myeloid Cell Function," Journal of Biological Chemistry, 2018, vol. 293, No. 32, pp. 12620-12633.
Extended European Search Report for European Application No. 19860614.7, mailed Jun. 3, 2022, 11 Pages.
International Preliminary Report on Patentability for International Application No. PCT/US2019/050575, mailed Mar. 25, 2021, 07 Pages.
Kobayashi M., et al., "TREM2/DAP12 Signal Elicits Proinflammatory Response in Microglia and Exacerbates Neuropathic Pain," The Journal of Neuroscience, Oct. 26, 2016, vol. 36, No. 43, pp. 11138-11150.
Leyns C.E.G et al., "TREM2 Deficiency Attenuates Neuroinflammation and Protects Against Neurodegeneration in a Mouse Model of Tauopathy," Proceedings of the National Academy of Sciences (PNAS), Oct. 24, 2017, vol. 114, No. 43, pp. 11524-11529.
Office Action for European Patent Application No. 19860614.7, mailed on Jun. 22, 2022, 1 page.
Satoh J-I., et al., "A Survey of TREM2 Antibodies Reveals Neuronal but not Microglial Staining in Formalin-Fixed Paraffin-Embedded Postmortem Alzheimer's Brain Tissues," Alzheimer's Research Therapy, Jul. 8, 2013, vol. 5, No. 30, pp. 1-3.
Wang S., et al., "Anti-Human TREM2 Induces Microglia Proliferation and Reduces Pathology in an Alzheimer's Disease Model," Journal of Experimental Medicine, 2020, vol. 217, No. 9, pp. 1-19.

\* cited by examiner

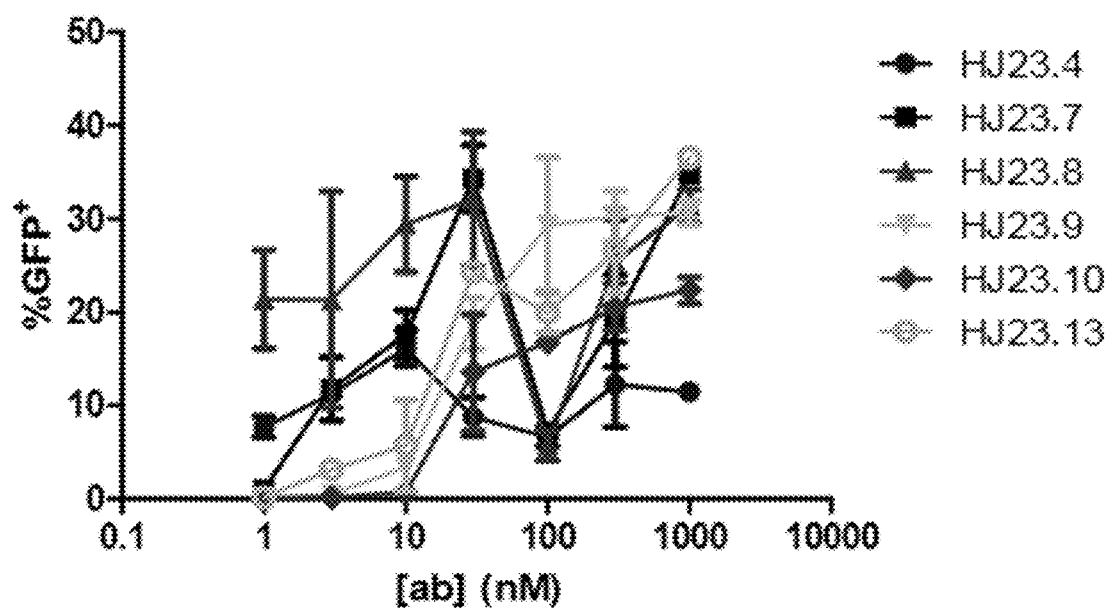

ANTI-TREM-2 AGONIST ANTIBODIES

CROSS-REFERENCE TO RELATED APPLICATIONS

This application claims priority to U.S. Provisional Application No. 62/729,458, filed Sep. 11, 2018, the disclosures of which are incorporated herein by reference in their entirety.

REFERENCE TO A SEQUENCE LISTING

This application contains a Sequence Listing that has been submitted in ASCII format via EFS-Web and is hereby incorporated by reference in its entirety. The ASCII copy, created on Sep. 10, 2019, is named Sequence_Listing_ST25.txt, and is 20 KB bytes in size.

BACKGROUND

TREM-2, also known as triggering receptor expressed on myeloid cells 2, is a protein that in humans is encoded by TREM2. TREM-2 is a receptor of the innate immune system expressed on microglia, macrophages, dendritic cells, and osteoclasts. TREM-2 is a member of the immunoglobulin superfamily. When triggered, it signals through the transmembrane adapter protein TYROBP/DAP12 to activate phagocytosis of pathogens and cellular debris as well as support cellular metabolic function, survival, and proliferation. Anti-inflammatory properties of TREM-2 have also been described, whereby TREM-2 suppresses expression and secretion of inflammatory cytokines in macrophages and microglia. Alternative splicing results in transcript variants encoding different isoforms of TREM-2, and missense mutations in TREM2 result in TREM-2 functional variants with increased or decreased signaling and/or increased or decreased affinity for putative ligands, as well as loss-of-function variants.

TREM-2-dependent phenotypes in mouse models point to an important role for TREM-2 in regulating the response of the innate immune system. Furthermore, elevations in the CSF levels of soluble TREM-2 fragments implicate changes in inflammatory pathways as occurring coincident with markers of neuronal damage in many diseases.

Accordingly, there is a need for antibodies that specifically bind TREM-2 and modulate its activities in various cell types, such as microglia, macrophages, dendritic cells, and osteoclasts.

SUMMARY

The present disclosure encompasses an isolated anti-TREM-2 antibody comprising (a) a light chain variable region comprising an L1 derived from SEQ ID NO: 1, an L2 derived from SEQ ID NO: 1, an L3 derived from of SEQ ID NO: 1, or any combination thereof; and/or (b) a heavy chain variable region comprising an H1 derived from SEQ ID NO: 2, an H2 derived from SEQ ID NO: 2, an H3 derived from of SEQ ID NO: 2, or any combination thereof. Compositions comprising the antibody, including but not limited to pharmaceutical compositions, are contemplated herein. In certain embodiments the antibody is a humanized antibody.

In another aspect, the present disclosure encompasses an isolated anti-TREM-2 antibody comprising (a) a light chain variable region comprising an L1 of SEQ ID NO: 3, an L2 comprising the amino acid sequence IVS, an L3 of SEQ ID NO: 4, or any combination thereof; and/or (b) a heavy chain variable region comprising an H1 comprising SEQ ID NO: 5, an H2 comprising SEQ ID NO: 6, an H3 comprising SEQ ID NO: 7, or any combination thereof. Compositions comprising the antibody, including but not limited to pharmaceutical compositions, are contemplated herein. In certain embodiments the antibody is a humanized antibody.

In another aspect, the present disclosure encompasses an isolated anti-TREM-2 antibody comprising (a) a light chain variable region comprising an L1 derived from SEQ ID NO: 8, an L2 derived from SEQ ID NO: 8, an L3 derived from of SEQ ID NO: 8, or any combination thereof; and/or (b) a heavy chain variable region comprising an H1 derived from SEQ ID NO: 9, an H2 derived from SEQ ID NO: 9, an H3 derived from of SEQ ID NO: 9, or any combination thereof. Compositions comprising the antibody, including but not limited to pharmaceutical compositions, are contemplated herein. In certain embodiments the antibody is a humanized antibody.

In another aspect, the present disclosure encompasses an isolated anti-TREM-2 antibody comprising (a) a light chain variable region comprising an L1 of SEQ ID NO: 10, an L2 comprising the amino acid sequence KVS, an L3 of SEQ ID NO: 11, or any combination thereof; and/or (b) a heavy chain variable region comprising an H1 comprising SEQ ID NO: 12, an H2 comprising SEQ ID NO: 13, an H3 comprising SEQ ID NO: 14, or any combination thereof. Compositions comprising the antibody, including but not limited to pharmaceutical compositions, are contemplated herein. In certain embodiments the antibody is a humanized antibody.

In another aspect, the present disclosure encompasses an isolated anti-TREM-2 antibody comprising (a) a light chain variable region comprising an L1 derived from SEQ ID NO: 15, an L2 derived from SEQ ID NO: 15, an L3 derived from of SEQ ID NO: 15, or any combination thereof; and/or (b) a heavy chain variable region comprising an H1 derived from SEQ ID NO: 16, an H2 derived from SEQ ID NO: 16, an H3 derived from of SEQ ID NO: 16, or any combination thereof. Compositions comprising the antibody, including but not limited to pharmaceutical compositions, are contemplated herein. In certain embodiments the antibody is a humanized antibody.

In another aspect, the present disclosure encompasses an isolated anti-TREM-2 antibody comprising (a) a light chain variable region comprising an L1 of SEQ ID NO: 17, an L2 comprising the amino acid sequence KVS, an L3 of SEQ ID NO: 18, or any combination thereof; and/or (b) a heavy chain variable region comprising an H1 comprising SEQ ID NO: 19, an H2 comprising SEQ ID NO: 22, an H3 comprising SEQ ID NO: 21, or any combination thereof. Compositions comprising the antibody, including but not limited to pharmaceutical compositions, are contemplated herein. In certain embodiments the antibody is a humanized antibody.

In another aspect, the present disclosure encompasses an isolated anti-TREM-2 antibody comprising (a) a light chain variable region comprising an L1 derived from SEQ ID NO: 22, an L2 derived from SEQ ID NO: 22, an L3 derived from of SEQ ID NO: 22, or any combination thereof; and/or (b) a heavy chain variable region comprising an H1 derived from SEQ ID NO: 23, an H2 derived from SEQ ID NO: 23, an H3 derived from of SEQ ID NO: 23, or any combination thereof. Compositions comprising the antibody, including but not limited to pharmaceutical compositions, are contemplated herein. In certain embodiments the antibody is a humanized antibody.

In another aspect, the present disclosure encompasses an isolated anti-TREM-2 antibody comprising (a) a light chain variable region comprising an L1 of SEQ ID NO: 24, an L2 comprising the amino acid sequence KVS, an L3 of SEQ ID NO: 25, or any combination thereof; and/or (b) a heavy chain variable region comprising an H1 comprising SEQ ID NO: 26, an H2 comprising SEQ ID NO: 27, an H3 comprising SEQ ID NO: 28, or any combination thereof. Compositions comprising the antibody, including but not limited to pharmaceutical compositions, are contemplated herein. In certain embodiments the antibody is a humanized antibody.

In another aspect, the present disclosure encompasses an isolated anti-TREM-2 antibody comprising (a) a light chain variable region comprising an L1 derived from SEQ ID NO: 29, an L2 derived from SEQ ID NO: 29, an L3 derived from of SEQ ID NO: 29, or any combination thereof; and/or (b) a heavy chain variable region comprising an H1 derived from SEQ ID NO: 30, an H2 derived from SEQ ID NO: 30, an H3 derived from of SEQ ID NO: 30, or any combination thereof. Compositions comprising the antibody, including but not limited to pharmaceutical compositions, are contemplated herein. In certain embodiments the antibody is a humanized antibody.

In another aspect, the present disclosure encompasses an isolated anti-TREM-2 antibody comprising (a) a light chain variable region comprising an L1 of SEQ ID NO: 31, an L2 comprising the amino acid sequence KVS, an L3 of SEQ ID NO: 32, or any combination thereof; and/or (b) a heavy chain variable region comprising an H1 comprising SEQ ID NO: 33, an H2 comprising SEQ ID NO: 34, an H3 comprising SEQ ID NO: 35, or any combination thereof. Compositions comprising the antibody, including but not limited to pharmaceutical compositions, are contemplated herein. In certain embodiments the antibody is a humanized antibody.

In another aspect, the present disclosure encompasses an isolated anti-TREM-2 antibody comprising (a) a light chain variable region comprising an L1 derived from SEQ ID NO: 36, an L2 derived from SEQ ID NO: 36, an L3 derived from of SEQ ID NO: 36, or any combination thereof; and/or (b) a heavy chain variable region comprising an H1 derived from SEQ ID NO: 37, an H2 derived from SEQ ID NO: 37, an H3 derived from of SEQ ID NO: 37, or any combination thereof. Compositions comprising the antibody, including but not limited to pharmaceutical compositions, are contemplated herein. In certain embodiments the antibody is a humanized antibody.

In another aspect, the present disclosure encompasses an isolated anti-TREM-2 antibody comprising (a) a light chain variable region comprising an L1 of SEQ ID NO: 38, an L2 comprising the amino acid sequence WAS, an L3 of SEQ ID NO: 39, or any combination thereof; and/or (b) a heavy chain variable region comprising an H1 comprising SEQ ID NO: 40, an H2 comprising SEQ ID NO: 41, an H3 comprising SEQ ID NO: 42, or any combination thereof. Compositions comprising the antibody, including but not limited to pharmaceutical compositions, are contemplated herein. In certain embodiments the antibody is a humanized antibody.

Other aspects and iterations of the invention are detailed below.

BRIEF DESCRIPTION OF THE FIGURES

FIG. 1 is a graph of a dose-response curve showing TREM-2 activation in response to treatment with anti-TREM-2 antibodies HJ23.4, HJ23.7, HJ23.8, HJ23.9, HJ23.10, and HJ23.13. TREM-2 activation is reported as % GFP (y-axis), relative to a negative control.

DETAILED DESCRIPTION

Applicants have discovered anti-TREM-2 antibodies that promote TREM-2 activation (referred to as "anti-TREM-2 agonist antibodies") and methods of using the anti-TREM-2 agonist antibodies therapeutically. For example, anti-TREM-2 antibodies disclosed herein may decrease neuronal degeneration in subjects with neurodegenerative diseases, such as Alzheimer's Disease (AD), frontotemporal dementia (FTD), amyotrophic lateral sclerosis (ALS), prion disease, and Parkinson's disease (PD). In particular, anti-TREM-2 antibodies disclosed herein may decrease neuronal degeneration in subjects with Aβ amyloidosis, thereby limiting amyloid-associated neurotoxicity. The present invention encompasses the discovery that anti-TREM-2 agonist antibodies provide a treatment for subjects with Aβ amyloidosis including, but not limited to, subjects diagnosed with a disease characterized by brain Aβ plaques, subjects diagnosed with a disease characterized by vascular Aβ plaques in the brain, subjects diagnosed with Aβ plaque-associated symptoms, subjects diagnosed with CAA-associated symptoms, subjects with clinical signs of Aβ amyloidosis that may or may not have Aβ plaque associated symptoms and/or CAA associated symptoms, subjects diagnosed with Alzheimer's disease, and subjects diagnosed with CAA. Methods for identifying clinical signs of Aβ amyloidosis in asymptomatic patients are known in the art and discussed below. Other uses are also detailed below.

I. Definitions

Unless expressly stated otherwise, "TREM-2" refers to "human TREM-2," and encompasses all isoforms, variants and functional fragments thereof. "Recombinant TREM-2" refers to TREM-2 encoded by a nucleic acid that has been introduced into a system (e.g. a prokaryotic cell, a eukaryotic cell, or a cell-free expression system) that supports expression of the nucleic acid and its translation into a protein. Methods for producing recombinant proteins are well-known in the art, and the production of recombinant TREM-2 disclosed herein is not limited to a particular system.

The term "subject" refers to a human, or to a non-human animal expressing human TREM-2.

The terms "treat," "treating," or "treatment" as used herein, refer to both therapeutic treatment and prophylactic or preventative measures, wherein the object is to prevent or slow down (lessen) an undesired physiological change or disease/disorder. Beneficial or desired clinical results include, but are not limited to, alleviation of symptoms, diminishment of extent of disease, stabilized (i.e., not worsening) state of disease, a delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the disease, condition, or disorder as well as those prone to have the disease, condition or disorder or those in which the disease, condition or disorder is to be prevented.

The term "Aβ" refers to peptides derived from a region in the carboxy terminus of a larger protein called amyloid precursor protein (APP). The gene encoding APP is located on chromosome 21. There are many forms of Aβ that may have toxic effects: Aβ peptides are typically 37-43 amino acid sequences long, though they can have truncations and modifications changing their overall size. They can be found in soluble and insoluble compartments, in monomeric, oligomeric and aggregated forms, intracellularly or extracellularly, and may be complexed with other proteins or molecules. The adverse or toxic effects of Aβ may be attributable to any or all of the above noted forms, as well as to others not described specifically. For example, two such Aβ isoforms include Aβ40 and Aβ42; with the Aβ42 isoform being particularly fibrillogenic or insoluble and associated with disease states.

"Aβ amyloidosis" is clinically defined as evidence of Aβ deposition in the brain or blood vessels of the brain, typically in the form of amyloid plaques or CAA. Diseases associated with Aβ amyloidosis include, but are not limited to, preclinical Alzheimer's disease, Alzheimer's disease (AD), cerebral amyloid angiopathy (CAA), Lewy body dementia, and inclusion body myositis. An "increased risk of developing a disease associated with Aβ amyloidosis" refers to a risk that is elevated over the expected risk given the subject's age, family history, genetic status and other known risk factors.

A "clinical sign of Aβ amyloidosis" refers to a measure of Aβ deposition known in the art. Clinical signs of Aβ amyloidosis may include, but are not limited to, Aβ deposition identified by amyloid imaging (e.g. PiB PET, fluorbetapir, or other imaging methods known in the art) or by decreased cerebrospinal fluid (CSF) Aβ42 or Aβ42/40 ratio. See, for example, Klunk W E et al. *Ann Neurol* 55(3) 2004, and Fagan A M et al. *Ann Neurol* 59(3) 2006, each hereby incorporated by reference in its entirety. Clinical signs of Aβ amyloidosis may also include measurements of the metabolism of Aβ, in particular measurements of Aβ42 metabolism alone or in comparison to measurements of the metabolism of other Aβ variants (e.g. Aβ37, Aβ38. Aβ39, Aβ40, and/or total Aβ), as described in U.S. patent Ser. Nos. 14/366,831, 14/523,148 and 14/747,453, each hereby incorporated by reference in its entirety. Additional methods are described in Albert et al. *Alzheimer's & Dementia* 2007 Vol. 7, pp. 170-179; McKhann et al., *Alzheimer's & Dementia* 2007 Vol. 7, pp. 263-269; and Sperling et al. *Alzheimer's & Dementia* 2007 Vol. 7, pp. 280-292, each hereby incorporated by reference in its entirety. Importantly, a subject with clinical signs of Aβ amyloidosis may or may not have symptoms associated with Aβ deposition. Yet subjects with clinical signs of Aβ amyloidosis are at an increased risk of developing a disease associated with Aβ amyloidosis.

An "Aβ plaque associated symptom" or a "CAA associated symptom" refers to any symptom caused by or associated with the formation of amyloid plaques or CAA, respectively, being composed of regularly ordered fibrillar aggregates called amyloid fibrils. Exemplary Aβ plaque associated symptoms may include, but are not limited to, neuronal degeneration, impaired cognitive function, impaired memory, altered behavior, emotional dysregulation, seizures, impaired nervous system structure or function, and an increased risk of development or worsening of Alzheimer's disease or CAA. Neuronal degeneration may include a change in structure of a neuron (including molecular changes such as intracellular accumulation of toxic proteins, protein aggregates, etc. and macro level changes such as change in shape or length of axons or dendrites, change in myelin sheath composition, loss of myelin sheath, etc.), a change in function of a neuron, a loss of function of a neuron, death of a neuron, or any combination thereof. Impaired cognitive function may include but is not limited to difficulties with memory, attention, concentration, language, abstract thought, creativity, executive function, planning, and organization. Altered behavior may include, but is not limited to, physical or verbal aggression, impulsivity, decreased inhibition, apathy, decreased initiation, changes in personality, abuse of alcohol, tobacco or drugs, and other addiction-related behaviors. Emotional dysregulation may include, but is not limited to, depression, anxiety, mania, irritability, and emotional incontinence. Seizures may include but are not limited to generalized tonic-clonic seizures, complex partial seizures, and non-epileptic, psychogenic seizures. Impaired nervous system structure or function may include, but is not limited to, hydrocephalus, Parkinsonism, sleep disorders, psychosis, impairment of balance and coordination. This may include motor impairments such as monoparesis, hemiparesis, tetraparesis, ataxia, ballismus and tremor. This also may include sensory loss or dysfunction including olfactory, tactile, gustatory, visual and auditory sensation. Furthermore, this may include autonomic nervous system impairments such as bowel and bladder dysfunction, sexual dysfunction, blood pressure and temperature dysregulation. Finally, this may include hormonal impairments attributable to dysfunction of the hypothalamus and pituitary gland such as deficiencies and dysregulation of growth hormone, thyroid stimulating hormone, lutenizing hormone, follicle stimulating hormone, gonadotropin releasing hormone, prolactin, and numerous other hormones and modulators.

The term "antibody," as used herein, is used in the broadest sense and encompasses various antibody and antibody-like structures, including but not limited to full-length monoclonal, polyclonal, and multispecific (e.g., bispecific, trispecific, etc.) antibodies, as well as heavy chain antibodies and antibody fragments provided they exhibit the desired antigen-binding activity. The domain(s) of an antibody that is involved in binding an antigen is referred to as a "variable region" or "variable domain," and is described in further detail below. A single variable domain may be sufficient to confer antigen-binding specificity. Preferably, but not necessarily, antibodies useful in the discovery are produced recombinantly. Antibodies may or may not be glycosylated, though glycosylated antibodies may be preferred. An "isolated" antibody is one which has been separated from a component of its natural environment. In some embodiments, an antibody is purified to greater than 95% or 99% purity as determined by methods known in the art.

In addition to antibodies described herein, it may be possible to design an antibody mimetic or an aptamer using methods known in the art that functions substantially the same as an antibody of the invention. An "antibody mimetic" refers to a polypeptide or a protein that can specifically bind to an antigen but is not structurally related to an antibody. Antibody mimetics have a mass of about 3 kDa to about 20 kDa. Non-limiting examples of antibody mimetics are affibody molecules, affilins, affimers, alphabodies, anticalins, avimers, DARPins, and monobodies. Aptamers are a class of small nucleic acid ligands that are composed of RNA or single-stranded DNA oligonucleotides and have high specificity and affinity for their targets. Aptamers interact with and bind to their targets through structural recognition, a process similar to that of an antigen-antibody reaction. Aptamers have a lower molecular weight than antibodies, typically about 8-25 kDa.

The terms "full length antibody" and "intact antibody" may be used interchangeably, and refer to an antibody having a structure substantially similar to a native antibody structure or having heavy chains that contain an Fc region as defined herein. The basic structural unit of a native antibody comprises a tetramer. Each tetramer is composed of two identical pairs of polypeptide chains, each pair having one "light" chain (about 25 kDa) and one "heavy" chain (about 50-70 kDa). Light chains are classified as gamma, mu, alpha, and lambda. Heavy chains are classified as gamma, mu, alpha, delta, or epsilon, and define the antibody's isotype as IgG, IgM. IgA, IgD and IgE, respectively. The amino-terminal portion of each light and heavy chain includes a variable region of about 100 to 110 or more amino acid sequences primarily responsible for antigen recognition (VL and VH, respectively). The carboxy-terminal portion of each chain defines a constant region primarily responsible for effector function. Within light and heavy chains, the variable and constant regions are joined by a "J" region of about 12 or more amino acid sequences, with the heavy chain also including a "D" region of about 10 more amino acid sequences. Intact antibodies are properly cross-linked via disulfide bonds, as is known in the art.

The variable domains of the heavy chain and light chain of an antibody generally have similar structures, with each domain comprising four conserved framework regions (FRs) and three hypervariable regions (HVRs). (See, e.g., Kindt et al. *Kuby Immunology*, 6th ed., W.H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., *J. Immunol.* 150:880-887 (1993); Clarkson et al., *Nature* 352:624-628 (1991).

"Framework region" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence: FR1-HVR1-FR2-HVR2-FR3-HVR3-FR4. The FR domains of a heavy chain and a light chain may differ, as is known in the art.

The term "hypervariable region" or "HVR" as used herein refers to each of the regions of a variable domain which are hypervariable in sequence (also commonly referred to as "complementarity determining regions" or "CDR") and/or form structurally defined loops ("hypervariable loops") and/or contain the antigen-contacting residues ("antigen contacts"). Generally, antibodies comprise six HVRs: three in the VH (H1, H2, H3), and three in the VL (L1, L2, L3). As used herein, "an HVR derived from a variable region" refers to an HVR that has no more than two amino acid substitutions, as compared to the corresponding HVR from the original variable region. Exemplary HVRs herein include: (a) hypervariable loops occurring at amino acid residues 26-32 (L1), 50-52 (L2), 91-96 (L3), 26-32 (H1), 53-55 (H2), and 96-101 (H3) (Chothia and Lesk, *J. Mol. Biol.* 196:901-917 (1987)); (b) CDRs occurring at amino acid residues 24-34 (L1), 50-56 (L2), 89-97 (L3), 31-35b (H1), 50-65 (H2), and 95-102 (H3) (Kabat et al., *Sequences of Proteins of Immunological Interest*, 5th Ed. Public Health Service, National Institutes of Health, Bethesda, Md. (1991)); (c) antigen contacts occurring at amino acid residues 27c-36 (L1), 46-55 (L2), 89-96 (L3), 30-35b (H1), 47-58 (H2), and 93-101 (H3) (MacCallum et al. *J. Mol. Biol.* 262: 732-745 (1996)); (d) CDR1-IMGT (positions 27-38), CDR2-IMGT (positions 56-65), and CDR3-IMGT regions (positions 105-116 or 105-117), which are based on IMGT unique numbering (Lefranc, "The IMGT unique numbering for Immunoglobulins, T cell receptors and Ig-like domains," The Immunologist, 1999, 7: 132-136; Lefranc et al., *Nucleic Acids Research*, 2009, 37(Database issue): D1006-D1012; Ehrenmann et al., "Chapter 2: Standardized Sequence and Structure Analysis of Antibody Using IMGT," in *Antibody Engineering Volume* 2, Eds. Roland E. Kontermann and Stefan Dubel, 2010, Springer-Verlag Berlin Heidelberg, doi: 10.1007/978-3-642-01147-4, and (e) combinations of (a), (b), (c), and/or (d), as defined below for various antibodies of this disclosure. Unless otherwise indicated, HVR residues and other residues in the variable domain (e.g., FR residues) that are assigned sequence identification numbers are numbered based on IMGT unique numbering, supra.

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., *Sequences of Proteins of Immunological Interest*, 5th Ed. Public Health Service. National Institutes of Health, Bethesda, Md., 1991.

A "variant Fc region" comprises an amino acid sequence that can differ from that of a native Fc region by virtue of one or more amino acid substitution(s) and/or by virtue of a modified glycosylation pattern, as compared to a native Fc region or to the Fc region of a parent polypeptide. In an example, a variant Fc region can have from about one to about ten amino acid substitutions, or from about one to about five amino acid substitutions in a native sequence Fc region or in the Fc region of the parent polypeptide. The variant Fc region herein may possess at least about 80% homology, at least about 90% homology, or at least about 95% homology with a native sequence Fc region and/or with an Fc region of a parent polypeptide.

An "antibody fragment" refers to a molecule other than an intact antibody that comprises a portion of an intact antibody that binds the antigen to which the intact antibody binds. Non-limiting examples of antibody fragments include but are not limited to Fv, Fab. Fab', Fab'-SH, F(ab')$_2$; single-chain forms of antibodies and higher order variants thereof: single-domain antibodies, and multispecific antibodies formed from antibody fragments.

Single-chain forms of antibodies, and their higher order forms, may include, but are not limited to, single-domain antibodies, single chain variant fragments (scFvs), divalent scFvs (di-scFvs), trivalent scFvs (tri-scFvs), tetravalent scFvs (tetra-scFvs), diabodies, and triabodies and tetrabodies. ScFv's are comprised of heavy and light chain variable regions connected by a linker. In most instances, but not all, the linker may be a peptide. A linker peptide is preferably from about 5 to 30 amino acids in length, or from about 10 to 25 amino acids in length. Typically, the linker allows for stabilization of the variable domains without interfering with the proper folding and creation of an active binding site. In preferred embodiments, a linker peptide is rich in glycine, as well as serine or threonine. ScFvs can be used to facilitate phage display or can be used for flow cytometry, immunohistochemistry, or as targeting domains. Methods of making and using scFvs are known in the art. ScFvs may also be conjugated to a human constant domain (e.g. a heavy constant domain is derived from an IgG domain, such as IgG1, IgG2, IgG3, or IgG4, or a heavy chain constant domain derived from an IgA, IgM, or IgE). Diabodies, triabodies, and tetrabodies and higher order variants are typically created by varying the length of the linker peptide from zero to several amino acids. Alternatively, it is also well known in the art that multivalent binding antibody variants can be generated using self-assembling units linked to the variable domain.

A "single-domain antibody" refers to an antibody fragment consisting of a single, monomeric variable antibody domain.

Multispecific antibodies include bi-specific antibodies, tri-specific, or antibodies of four or more specificities. Multispecific antibodies may be created by combining the heavy and light chains of one antibody with the heavy and light chains of one or more other antibodies. These chains can be covalently linked.

"Monoclonal antibody" refers to an antibody that is derived from a single copy or clone, including e.g., any eukaryotic, prokaryotic, or phage clone. "Monoclonal antibody" is not limited to antibodies produced through hybridoma technology. Monoclonal antibodies can be produced using hybridoma techniques well known in the art, as well as recombinant technologies, phage display technologies, synthetic technologies or combinations of such technologies and other technologies readily known in the art. Furthermore, the monoclonal antibody may be labeled with a detectable label, immobilized on a solid phase and/or conjugated with a heterologous compound (e.g., an enzyme or toxin) according to methods known in the art.

A "heavy chain antibody" refers to an antibody that consists of two heavy chains. A heavy chain antibody may be an IgG-like antibody from camels, llamas, alpacas, sharks, etc. . . . or an IgNAR from a cartiliaginous fish.

A "humanized antibody" refers to a non-human antibody that has been modified to reduce the risk of the non-human antibody eliciting an immune response in humans following administration but retains similar binding specificity and affinity as the starting non-human antibody. A humanized antibody binds to the same or similar epitope as the non-human antibody. The term "humanized antibody" includes an antibody that is composed partially or fully of amino acid sequences derived from a human antibody germline by altering the sequence of an antibody having non-human hypervariable regions ("HVR"). The simplest such alteration may consist simply of substituting the constant region of a human antibody for the murine constant region, thus resulting in a human/murine chimera which may have sufficiently low immunogenicity to be acceptable for pharmaceutical use. Preferably, the variable region of the antibody is also humanized by techniques that are by now well known in the art. For example, the framework regions of a variable region can be substituted by the corresponding human framework regions, while retaining one, several, or all six non-human HVRs. Some framework residues can be substituted with corresponding residues from a non-human VL domain or VH domain (e.g., the non-human antibody from which the HVR residues are derived). e.g., to restore or improve specificity or affinity of the humanized antibody. Substantially human framework regions have at least about 75% homology with a known human framework sequence (i.e. at least about 75%, at least about 80%, at least about 85%, at least about 90%, at least about 95%, or at least about 99% sequence identity). HVRs may also be randomly mutated such that binding activity and affinity for the antigen is maintained or enhanced in the context of fully human germline framework regions or framework regions that are substantially human. As mentioned above, it is sufficient for use in the methods of this discovery to employ an antibody fragment. Further, as used herein, the term "humanized antibody" refers to an antibody comprising a substantially human framework region, at least one HVR from a nonhuman antibody, and in which any constant region present is substantially human. Substantially human constant regions have at least about 90% with a known human constant sequence (i.e. about 90%, about 95%, or about 99% sequence identity). Hence, all parts of a humanized antibody, except possibly the HVRs, are substantially identical to corresponding pairs of one or more germline human immunoglobulin sequences.

If desired, the design of humanized immunoglobulins may be carried out as follows, or using similar methods familiar to those with skill in the art (for example, see Almagro, et al. *Front. Biosci.* 2008, 13(5): 1619-33). A murine antibody variable region is aligned to the most similar human germline sequences (e.g. by using BLAST or similar algorithm). The CDR residues from the murine antibody sequence are grafted into the similar human "acceptor" germline. Subsequently, one or more positions near the CDRs or within the framework (e.g., Vernier positions) may be reverted to the original murine amino acid in order to achieve a humanized antibody with similar binding affinity to the original murine antibody. Typically, several versions of humanized antibodies with different reversion mutations are generated and empirically tested for activity. The humanized antibody variant with properties most similar to the parent murine antibody and the fewest murine framework reversions is selected as the final humanized antibody candidate.

II. Anti-TREM-2 Antibody

An "anti-TREM-2 antibody." as used herein, refers to an isolated antibody that binds to recombinant human TREM-2 with an affinity constant or affinity of interaction (KD) between about 0.1 μM to about 10 μM, preferably about 0.1 μM to about 1 μM, more preferably about 0.1 μM to about 100 nM. Methods for determining the affinity of an antibody for an antigen are known in the art, and further illustrated in the Examples. Anti-TREM-2 antibodies useful herein include those which are suitable for administration to a subject in a therapeutic amount.

Anti-TREM-2 antibodies disclosed herein are agonist antibodies, meaning the antibodies bind TREM-2 in a manner that mimics the binding of a natural ligand, resulting in antibody-mediated downstream signaling or agonism.

Anti-TREM-2 antibodies disclosed herein can be described or specified in terms of the epitope(s) that they recognize or bind. The portion of a target polypeptide that specifically interacts with the antigen binding domain of an antibody is an "epitope." TREM-2 can comprise any number of epitopes, depending on the source of the protein (e.g. mouse, rat, cynomolgus monkey, human, etc.), variants (e.g., R47H, R62H. R62C, G55R, A28V, etc.), conformational state of the protein (e.g., aggregated, insoluble, soluble, post-translationally modified, etc.) and location of the protein (e.g., intracellular, extracellular, complexed with other proteins or molecules in particle, in amyloid plaque, etc.). Furthermore, it should be noted that an "epitope" on TREM-2 can be a linear epitope or a conformational epitope, and in both instances can include non-polypeptide elements, e.g., an epitope can include a carbohydrate or lipid side chain. The term "affinity" refers to a measure of the strength of the binding of an individual epitope with an antibody's antigen binding site.

Anti-TREM-2 antibodies disclosed herein can also be described or specified in terms of their cross-reactivity. The term "cross-reactivity" refers to the ability of an antibody, specific for one antigen, to react with a second antigen; a measure of relatedness between two different antigenic substances. Thus, an antibody is cross-reactive if it binds to an epitope other than the one that induced its formation. The cross-reactive epitope generally contains many of the same complementary structural features as the inducing epitope, and in some cases, can actually fit better than the original. For example, certain antibodies have some degree of cross-reactivity, in that they bind related, but non-identical epitopes, e.g., epitopes with at least about 85%, at least about 90%, or at least about 95% identity (as calculated using methods known in the art) to a reference epitope. An antibody can be said to have little or no cross-reactivity if it does not bind epitopes with less than about 95%, less than about 90%, or less than about 85% identity to a reference epitope. An antibody can be deemed "highly specific" for a certain epitope, if it does not bind any other analog, ortholog, or homolog of that epitope.

Anti-TREM-2 antibodies of this disclosure may or may not have a variant Fc region. In some examples, an Fc region can be modified to have increased or decreased affinity for an Fc receptor on a microglial cell and/or an altered glycosylation pattern.

In one example, an anti-TREM-2 antibody comprises a VL that has one or more HVRs derived from SEQ ID NO: 1 or a VH that has one or more HVRs derived from SEQ ID NO: 2. The HVR derived from SEQ ID NO: 1 may be L1, L2, L3, or any combination thereof. In certain embodiments, the VL may comprise an L1 of SEQ ID NO: 3, an L2 comprising the amino acid sequence IVS, an L3 of SEQ ID NO: 4, or any combination thereof (e.g. antibodies 1-7 in Table A). The HVR derived from SEQ ID NO: 2 may be H1, H2, H3, or any combination thereof. In certain embodiments, the VH may comprise an H1 of SEQ ID NO: 5, an H2 of SEQ ID NO: 6, an H3 of SEQ ID NO: 7, or any combination thereof (e.g. antibodies 8-14 in Table A). The antibody comprising one or more HVRs derived from SEQ ID NO: 2 may further comprise a light chain variable region (VL) comprising one or more HVRs derived from SEQ ID NO: 1. The HVR may be L1, L2, L3, or any combination thereof. In a preferred embodiment, the VL may comprise an L1 of SEQ ID NO: 3, an L2 comprising the amino acid sequence IVS, an L3 of SEQ ID NO: 4, or any combination thereof (e.g. antibodies 15-63 in Table A). In various embodiments above, the antibody may be a humanized antibody, or the antibody may have a VL with 90, 91, 92, 93, 94, 95, 96, 97, 98, 99, or 100% identity to SEQ ID NO: 1 and/or a VH with 90, 91, 92, 93, 94, 95, 96, 97, 98, 99 or 100% identity to SEQ ID NO: 2. In each of the above embodiments, the anti-TREM-2 antibody may optionally comprise one or more constant regions, or a portion of a constant region, that is substantially human (i.e. at least 90%, 95%, or 99% sequence identity with a known human framework sequence). The present disclosure also encompasses the corresponding nucleic acid sequences of SEQ ID NO: 1, 2, 3, 4, 5, 6, and 7, which can readily be determined by one of skill in the art, and may be incorporated into a vector or other large DNA molecule, such as a chromosome, in order to express an antibody of the disclosure.

In another example, an anti-TREM-2 antibody comprises a VL that has one or more HVRs derived from SEQ ID NO: 8 or a VH that has one or more HVRs derived from SEQ ID NO: 9. The HVR derived from SEQ ID NO: 8 may be L1, L2, L3, or any combination thereof. In certain embodiments, the VL may comprise an L1 of SEQ ID NO: 10, an L2 comprising the amino acid sequence KVS, an L3 of SEQ ID NO: 11, or any combination thereof (e.g. antibodies 64-70 in Table A). The HVR derived from SEQ ID NO: 9 may be H1, H2, H3, or any combination thereof. In certain embodiments, the VH may comprise an H1 of SEQ ID NO: 12, an H2 of SEQ ID NO: 13, an H3 of SEQ ID NO: 14, or any combination thereof (e.g. antibodies 71-77 in Table A). The antibody comprising one or more HVRs derived from SEQ ID NO: 9 may further comprise a light chain variable region (VL) comprising one or more HVRs derived from SEQ ID NO: 8. The HVR may be L1, L2, L3, or any combination thereof. In a preferred embodiment, the VL may comprise an L1 of SEQ ID NO: 10, an L2 comprising the amino acid sequence KVS, an L3 of SEQ ID NO: 11, or any combination thereof (e.g. antibodies 78-126 in Table A). In various embodiments above, the antibody may be a humanized antibody, or the antibody may have a VL with 90, 91, 92, 93, 94, 95, 96, 97, 98, 99, or 100% identity to SEQ ID NO: 9 and/or a VH with 90, 91, 92, 93, 94, 95, 96, 97, 98, 99 or 100% identity to SEQ ID NO: 10. In each of the above embodiments, the anti-TREM-2 antibody may optionally comprise one or more constant regions, or a portion of a constant region, that is substantially human (i.e. at least 90%, 95%, or 99% sequence identity with a known human framework sequence). The present disclosure also encompasses the corresponding nucleic acid sequences of SEQ ID NO: 8, 9, 10, 11, 12, 13, and 14, which can readily be determined by one of skill in the art, and may be incorporated into a vector or other large DNA molecule, such as a chromosome, in order to express an antibody of the disclosure.

In another example, an anti-TREM-2 antibody comprises a VL that has one or more HVRs derived from SEQ ID NO: 15 or a VH that has one or more HVRs derived from SEQ ID NO: 16. The HVR derived from SEQ ID NO: 15 may be L1, L2, L3, or any combination thereof. In certain embodiments, the VL may comprise an L1 of SEQ ID NO: 17, an L2 comprising the amino acid sequence KVS, an L3 of SEQ ID NO: 18, or any combination thereof (e.g. antibodies 127-133 in Table A). The HVR derived from SEQ ID NO: 16 may be H1, H2, H3, or any combination thereof. In certain embodiments, the VH may comprise an H1 of SEQ ID NO: 19, an H2 of SEQ ID NO: 20, an H3 of SEQ ID NO: 21, or any combination thereof (e.g. antibodies 134-140 in Table A). The antibody comprising one or more HVRs derived from SEQ ID NO: 16 may further comprise a light chain variable region (VL) comprising one or more HVRs derived from SEQ ID NO: 15. The HVR may be L1, L2, L3, or any combination thereof. In a preferred embodiment, the VL may comprise an L1 of SEQ ID NO: 17, an L2 comprising the amino acid sequence KVS, an L3 of SEQ ID NO: 18, or any combination thereof (e.g. antibodies 141-189 in Table A). In various embodiments above, the antibody may be a humanized antibody, or the antibody may have a VL with 90, 91, 92, 93, 94, 95, 96, 97, 98, 99, or 100% identity to SEQ ID NO: 15 and/or a VH with 90, 91, 92, 93, 94, 95, 96, 97, 98, 99 or 100% identity to SEQ ID NO: 16. In each of the above embodiments, the anti-TREM-2 antibody may optionally comprise one or more constant regions, or a portion of a constant region, that is substantially human (i.e. at least 90%, 95%, or 99% sequence identity with a known human framework sequence). The present disclosure also encompasses the corresponding nucleic acid sequences of SEQ ID NO: 15, 16, 17, 18, 19, 20, and 21, which can readily be determined by one of skill in the art, and may be incorporated into a vector or other large DNA molecule, such as a chromosome, in order to express an antibody of the disclosure.

In another example, an anti-TREM-2 antibody comprises a VL that has one or more HVRs derived from SEQ ID NO:

22 or a VH that has one or more HVRs derived from SEQ ID NO: 23. The HVR derived from SEQ ID NO: 22 may be L1, L2, L3, or any combination thereof. In certain embodiments, the VL may comprise an L1 of SEQ ID NO: 24, an L2 comprising the amino acid sequence KVS, an L3 of SEQ ID NO: 25, or any combination thereof (e.g. antibodies 190-196 in Table A). The HVR derived from SEQ ID NO: 23 may be H1, H2, H3, or any combination thereof. In certain embodiments, the VH may comprise an H1 of SEQ ID NO: 26, an H2 of SEQ ID NO: 27, an H3 of SEQ ID NO: 28, or any combination thereof (e.g. antibodies 197-203 in Table A). The antibody comprising one or more HVRs derived from SEQ ID NO: 23 may further comprise a light chain variable region (VL) comprising one or more HVRs derived from SEQ ID NO: 22. The HVR may be L1, L2, L3, or any combination thereof. In a preferred embodiment, the VL may comprise an L1 of SEQ ID NO: 24, an L2 comprising the amino acid sequence KVS, an L3 of SEQ ID NO: 25, or any combination thereof (e.g. antibodies 204-252 in Table A). In various embodiments above, the antibody may be a humanized antibody, or the antibody may have a VL with 90, 91, 92, 93, 94, 95, 96, 97, 98, 99, or 100% identity to SEQ ID NO: 22 and/or a VH with 90, 91, 92, 93, 94, 95, 96, 97, 98, 99 or 100% identity to SEQ ID NO: 23. In each of the above embodiments, the anti-TREM-2 antibody may optionally comprise one or more constant regions, or a portion of a constant region, that is substantially human (i.e. at least 90%, 95%, or 99% sequence identity with a known human framework sequence). The present disclosure also encompasses the corresponding nucleic acid sequences of SEQ ID NO: 22, 23, 24, 25, 26, 27, and 28, which can readily be determined by one of skill in the art, and may be incorporated into a vector or other large DNA molecule, such as a chromosome, in order to express an antibody of the disclosure.

In another example, an anti-TREM-2 antibody comprises a VL that has one or more HVRs derived from SEQ ID NO: 29 or a VH that has one or more HVRs derived from SEQ ID NO: 30. The HVR derived from SEQ ID NO: 29 may be L1, L2, L3, or any combination thereof. In certain embodiments, the VL may comprise an L1 of SEQ ID NO: 31, an L2 comprising the amino acid sequence KVS, an L3 of SEQ ID NO: 32, or any combination thereof (e.g. antibodies 253-259 in Table A). The HVR derived from SEQ ID NO: 30 may be H1, H2, H3, or any combination thereof. In certain embodiments, the VH may comprise an H1 of SEQ ID NO: 33, an H2 of SEQ ID NO: 34, an H3 of SEQ ID NO: 35, or any combination thereof (e.g. antibodies 260-266 in Table A). The antibody comprising one or more HVRs derived from SEQ ID NO: 30 may further comprise a light chain variable region (VL) comprising one or more HVRs derived from SEQ ID NO: 29. The HVR may be L1, L2, L3, or any combination thereof. In a preferred embodiment, the VL may comprise an L1 of SEQ ID NO: 31, an L2 comprising the amino acid sequence KVS, an L3 of SEQ ID NO: 32, or any combination thereof (e.g. antibodies 267-315 in Table A). In various embodiments above, the antibody may be a humanized antibody, or the antibody may have a VL with 90, 91, 92, 93, 94, 95, 96, 97, 98, 99, or 100% identity to SEQ ID NO: 29 and/or a VH with 90, 91, 92, 93, 94, 95, 96, 97, 98, 99 or 100% identity to SEQ ID NO: 30. In each of the above embodiments, the anti-TREM-2 antibody may optionally comprise one or more constant regions, or a portion of a constant region, that is substantially human (i.e. at least 90%, 95%, or 99% sequence identity with a known human framework sequence). The present disclosure also encompasses the corresponding nucleic acid sequences of SEQ ID NO: 29, 30, 31, 32, 33, 34, and 35, which can readily be determined by one of skill in the art, and may be incorporated into a vector or other large DNA molecule, such as a chromosome, in order to express an antibody of the disclosure.

In another example, an anti-TREM-2 antibody comprises a VL that has one or more HVRs derived from SEQ ID NO: 36 or a VH that has one or more HVRs derived from SEQ ID NO: 37. The HVR derived from SEQ ID NO: 36 may be L1, L2, L3, or any combination thereof. In certain embodiments, the VL may comprise an L1 of SEQ ID NO: 38, an L2 comprising the amino acid sequence WAS, an L3 of SEQ ID NO: 39, or any combination thereof (e.g. antibodies 316-322 in Table A). The HVR derived from SEQ ID NO: 37 may be H1, H2, H3, or any combination thereof. In certain embodiments, the VH may comprise an H1 of SEQ ID NO: 40, an H2 of SEQ ID NO: 41, an H3 of SEQ ID NO: 42, or any combination thereof (e.g. antibodies 323-329 in Table A). The antibody comprising one or more HVRs derived from SEQ ID NO: 37 may further comprise a light chain variable region (VL) comprising one or more HVRs derived from SEQ ID NO: 36. The HVR may be L1, L2, L3, or any combination thereof. In a preferred embodiment, the VL may comprise an L1 of SEQ ID NO: 38, an L2 comprising the amino acid sequence WAS, an L3 of SEQ ID NO: 39, or any combination thereof (e.g. antibodies 330-378 in Table A). In various embodiments above, the antibody may be a humanized antibody, or the antibody may have a VL with 90, 91, 92, 93, 94, 95, 96, 97, 98, 99, or 100% identity to SEQ ID NO: 36 and/or a VH with 90, 91, 92, 93, 94, 95, 96, 97, 98, 99 or 100% identity to SEQ ID NO: 37. In each of the above embodiments, the anti-TREM-2 antibody may optionally comprise one or more constant regions, or a portion of a constant region, that is substantially human (i.e. at least 90%, 95%, or 99% sequence identity with a known human framework sequence). The present disclosure also encompasses the corresponding nucleic acid sequences of SEQ ID NO: 36, 37, 38, 39, 40, 41, and 42, which can readily be determined by one of skill in the art, and may be incorporated into a vector or other large DNA molecule, such as a chromosome, in order to express an antibody of the disclosure.

In some embodiments, each of the exemplary antibodies described above may also contain a variant Fc region, including but not limited to a variant Fc region that is modified to alter the natural interaction with the microglia FcR.

TABLE A

| | Light Chain HVR | | | Heavy Chain HVR | | |
|---|---|---|---|---|---|---|
| Antibody | L1 | L2 | L3 | H1 | H2 | H3 |
| 1 | SEQ ID NO: 3 | | | | | |
| 2 | SEQ ID NO: 3 | IVS | | | | |
| 3 | SEQ ID NO: 3 | IVS | SEQ ID NO: 4 | | | |
| 4 | | IVS | | | | |

TABLE A-continued

| | Light Chain HVR | | | Heavy Chain HVR | | |
|---|---|---|---|---|---|---|
| Antibody | L1 | L2 | L3 | H1 | H2 | H3 |
| 5 | | IVS | SEQ ID NO: 4 | | | |
| 6 | | | SEQ ID NO: 4 | | | |
| 7 | SEQ ID NO: 3 | | SEQ ID NO: 4 | | | |
| 8 | | | | SEQ ID NO: 5 | | |
| 9 | | | | SEQ ID NO: 5 | SEQ ID NO: 6 | |
| 10 | | | | SEQ ID NO: 5 | SEQ ID NO: 6 | SEQ ID NO: 7 |
| 11 | | | | | SEQ ID NO: 6 | |
| 12 | | | | | SEQ ID NO: 6 | SEQ ID NO: 7 |
| 13 | | | | | | SEQ ID NO: 7 |
| 14 | | | | SEQ ID NO: 5 | | SEQ ID NO: 7 |
| 15 | SEQ ID NO: 3 | | | SEQ ID NO: 5 | | |
| 16 | SEQ ID NO: 3 | | | SEQ ID NO: 5 | SEQ ID NO: 6 | |
| 17 | SEQ ID NO: 3 | | | SEQ ID NO: 5 | SEQ ID NO: 6 | SEQ ID NO: 7 |
| 18 | SEQ ID NO: 3 | | | | SEQ ID NO: 6 | |
| 19 | SEQ ID NO: 3 | | | | SEQ ID NO: 6 | SEQ ID NO: 7 |
| 20 | SEQ ID NO: 3 | | | | | SEQ ID NO: 7 |
| 21 | SEQ ID NO: 3 | | | SEQ ID NO: 5 | | SEQ ID NO: 7 |
| 22 | SEQ ID NO: 3 | IVS | | SEQ ID NO: 5 | | |
| 23 | SEQ ID NO: 3 | IVS | | SEQ ID NO: 5 | SEQ ID NO: 6 | |
| 24 | SEQ ID NO: 3 | IVS | | SEQ ID NO: 5 | SEQ ID NO: 6 | SEQ ID NO: 7 |
| 25 | SEQ ID NO: 3 | IVS | | | SEQ ID NO: 6 | |
| 26 | SEQ ID NO: 3 | IVS | | | SEQ ID NO: 6 | SEQ ID NO: 7 |
| 27 | SEQ ID NO: 3 | IVS | | | | SEQ ID NO: 7 |
| 28 | SEQ ID NO: 3 | IVS | | SEQ ID NO: 5 | | SEQ ID NO: 7 |
| 29 | SEQ ID NO: 3 | IVS | SEQ ID NO: 4 | SEQ ID NO: 5 | | |
| 30 | SEQ ID NO: 3 | IVS | SEQ ID NO: 4 | SEQ ID NO: 5 | SEQ ID NO: 6 | |
| 31 | SEQ ID NO: 3 | IVS | SEQ ID NO: 4 | SEQ ID NO: 5 | SEQ ID NO: 6 | SEQ ID NO: 7 |
| 32 | SEQ ID NO: 3 | IVS | SEQ ID NO: 4 | | SEQ ID NO: 6 | |
| 33 | SEQ ID NO: 3 | IVS | SEQ ID NO: 4 | | SEQ ID NO: 6 | SEQ ID NO: 7 |
| 34 | SEQ ID NO: 3 | IVS | SEQ ID NO: 4 | | | SEQ ID NO: 7 |
| 35 | SEQ ID NO: 3 | IVS | SEQ ID NO: 4 | SEQ ID NO: 5 | | SEQ ID NO: 7 |
| 36 | | IVS | | SEQ ID NO: 5 | | |
| 37 | | IVS | | SEQ ID NO: 5 | SEQ ID NO: 6 | |
| 38 | | IVS | | SEQ ID NO: 5 | SEQ ID NO: 6 | SEQ ID NO: 7 |
| 39 | | IVS | | | SEQ ID NO: 6 | |
| 40 | | IVS | | | SEQ ID NO: 6 | SEQ ID NO: 7 |
| 41 | | IVS | | | | SEQ ID NO: 7 |
| 42 | | IVS | | SEQ ID NO: 5 | | SEQ ID NO: 7 |
| 43 | | IVS | SEQ ID NO: 4 | SEQ ID NO: 5 | | |
| 44 | | IVS | SEQ ID NO: 4 | SEQ ID NO: 5 | SEQ ID NO: 6 | |
| 45 | | IVS | SEQ ID NO: 4 | SEQ ID NO: 5 | SEQ ID NO: 6 | SEQ ID NO: 7 |
| 46 | | IVS | SEQ ID NO: 4 | | SEQ ID NO: 6 | |
| 47 | | IVS | SEQ ID NO: 4 | | SEQ ID NO: 6 | SEQ ID NO: 7 |
| 48 | | IVS | SEQ ID NO: 4 | | | SEQ ID NO: 7 |
| 49 | | IVS | SEQ ID NO: 4 | SEQ ID NO: 5 | | SEQ ID NO: 7 |
| 50 | | | SEQ ID NO: 4 | SEQ ID NO: 5 | | |
| 51 | | | SEQ ID NO: 4 | SEQ ID NO: 5 | SEQ ID NO: 6 | |
| 52 | | | SEQ ID NO: 4 | SEQ ID NO: 5 | SEQ ID NO: 6 | SEQ ID NO: 7 |
| 53 | | | SEQ ID NO: 4 | | SEQ ID NO: 6 | |
| 54 | | | SEQ ID NO: 4 | | SEQ ID NO: 6 | SEQ ID NO: 7 |
| 55 | | | SEQ ID NO: 4 | | | SEQ ID NO: 7 |
| 56 | | | SEQ ID NO: 4 | SEQ ID NO: 5 | | SEQ ID NO: 7 |
| 57 | SEQ ID NO: 3 | | SEQ ID NO: 4 | SEQ ID NO: 5 | | |
| 58 | SEQ ID NO: 3 | | SEQ ID NO: 4 | SEQ ID NO: 5 | SEQ ID NO: 6 | |
| 59 | SEQ ID NO: 3 | | SEQ ID NO: 4 | SEQ ID NO: 5 | SEQ ID NO: 6 | SEQ ID NO: 7 |
| 60 | SEQ ID NO: 3 | | SEQ ID NO: 4 | | SEQ ID NO: 6 | |
| 61 | SEQ ID NO: 3 | | SEQ ID NO: 4 | | SEQ ID NO: 6 | SEQ ID NO: 7 |
| 62 | SEQ ID NO: 3 | | SEQ ID NO: 4 | | | SEQ ID NO: 7 |
| 63 | SEQ ID NO: 3 | | SEQ ID NO: 4 | SEQ ID NO: 5 | | SEQ ID NO: 7 |
| 64 | SEQ ID NO: 10 | | | | | |
| 65 | SEQ ID NO: 10 | KVS | | | | |
| 66 | SEQ ID NO: 10 | KVS | SEQ ID NO: 11 | | | |
| 67 | | KVS | | | | |
| 68 | | KVS | SEQ ID NO: 11 | | | |
| 69 | | | SEQ ID NO: 11 | | | |
| 70 | SEQ ID NO: 10 | | SEQ ID NO: 11 | | | |
| 71 | | | | SEQ ID NO: 12 | | |
| 72 | | | | SEQ ID NO: 12 | SEQ ID NO: 13 | |
| 73 | | | | SEQ ID NO: 12 | SEQ ID NO: 13 | SEQ ID NO: 14 |
| 74 | | | | | SEQ ID NO: 13 | |
| 75 | | | | | SEQ ID NO: 13 | SEQ ID NO: 14 |
| 76 | | | | | | SEQ ID NO: 14 |
| 77 | | | | SEQ ID NO: 12 | | SEQ ID NO: 14 |
| 78 | SEQ ID NO: 10 | | | SEQ ID NO: 12 | | |
| 79 | SEQ ID NO: 10 | | | SEQ ID NO: 12 | SEQ ID NO: 13 | |
| 80 | SEQ ID NO: 10 | | | SEQ ID NO: 12 | SEQ ID NO: 13 | SEQ ID NO: 14 |

TABLE A-continued

| | Light Chain HVR | | | Heavy Chain HVR | | |
|---|---|---|---|---|---|---|
| Antibody | L1 | L2 | L3 | H1 | H2 | H3 |
| 81 | SEQ ID NO: 10 | | | | SEQ ID NO: 13 | |
| 82 | SEQ ID NO: 10 | | | | SEQ ID NO: 13 | SEQ ID NO: 14 |
| 83 | SEQ ID NO: 10 | | | | | SEQ ID NO: 14 |
| 84 | SEQ ID NO: 10 | | | SEQ ID NO: 12 | | SEQ ID NO: 14 |
| 85 | SEQ ID NO: 10 | KVS | | SEQ ID NO: 12 | | |
| 86 | SEQ ID NO: 10 | KVS | | SEQ ID NO: 12 | SEQ ID NO: 13 | |
| 87 | SEQ ID NO: 10 | KVS | | SEQ ID NO: 12 | SEQ ID NO: 13 | SEQ ID NO: 14 |
| 88 | SEQ ID NO: 10 | KVS | | | SEQ ID NO: 13 | |
| 89 | SEQ ID NO: 10 | KVS | | | SEQ ID NO: 13 | SEQ ID NO: 14 |
| 90 | SEQ ID NO: 10 | KVS | | | | SEQ ID NO: 14 |
| 91 | SEQ ID NO: 10 | KVS | | SEQ ID NO: 12 | | SEQ ID NO: 14 |
| 92 | SEQ ID NO: 10 | KVS | SEQ ID NO: 11 | SEQ ID NO: 12 | | |
| 93 | SEQ ID NO: 10 | KVS | SEQ ID NO: 11 | SEQ ID NO: 12 | SEQ ID NO: 13 | |
| 94 | SEQ ID NO: 10 | KVS | SEQ ID NO: 11 | SEQ ID NO: 12 | SEQ ID NO: 13 | SEQ ID NO: 14 |
| 95 | SEQ ID NO: 10 | KVS | SEQ ID NO: 11 | | SEQ ID NO: 13 | |
| 96 | SEQ ID NO: 10 | KVS | SEQ ID NO: 11 | | SEQ ID NO: 13 | SEQ ID NO: 14 |
| 97 | SEQ ID NO: 10 | KVS | SEQ ID NO: 11 | | | SEQ ID NO: 14 |
| 98 | SEQ ID NO: 10 | KVS | SEQ ID NO: 11 | SEQ ID NO: 12 | | SEQ ID NO: 14 |
| 99 | | KVS | | SEQ ID NO: 12 | | |
| 100 | | KVS | | SEQ ID NO: 12 | SEQ ID NO: 13 | |
| 101 | | KVS | | SEQ ID NO: 12 | SEQ ID NO: 13 | SEQ ID NO: 14 |
| 102 | | KVS | | | SEQ ID NO: 13 | |
| 103 | | KVS | | | SEQ ID NO: 13 | SEQ ID NO: 14 |
| 104 | | KVS | | | | SEQ ID NO: 14 |
| 105 | | KVS | | SEQ ID NO: 12 | | SEQ ID NO: 14 |
| 106 | | KVS | SEQ ID NO: 11 | SEQ ID NO: 12 | | |
| 107 | | KVS | SEQ ID NO: 11 | SEQ ID NO: 12 | SEQ ID NO: 13 | |
| 108 | | KVS | SEQ ID NO: 11 | SEQ ID NO: 12 | SEQ ID NO: 13 | SEQ ID NO: 14 |
| 109 | | KVS | SEQ ID NO: 11 | | SEQ ID NO: 13 | |
| 110 | | KVS | SEQ ID NO: 11 | | SEQ ID NO: 13 | SEQ ID NO: 14 |
| 111 | | KVS | SEQ ID NO: 11 | | | SEQ ID NO: 14 |
| 112 | | KVS | SEQ ID NO: 11 | SEQ ID NO: 12 | | SEQ ID NO: 14 |
| 113 | | | SEQ ID NO: 11 | SEQ ID NO: 12 | | |
| 114 | | | SEQ ID NO: 11 | SEQ ID NO: 12 | SEQ ID NO: 13 | |
| 115 | | | SEQ ID NO: 11 | SEQ ID NO: 12 | SEQ ID NO: 13 | SEQ ID NO: 14 |
| 116 | | | SEQ ID NO: 11 | | SEQ ID NO: 13 | |
| 117 | | | SEQ ID NO: 11 | | SEQ ID NO: 13 | SEQ ID NO: 14 |
| 118 | | | SEQ ID NO: 11 | | | SEQ ID NO: 14 |
| 119 | | | SEQ ID NO: 11 | SEQ ID NO: 12 | | SEQ ID NO: 14 |
| 120 | SEQ ID NO: 10 | | SEQ ID NO: 11 | SEQ ID NO: 12 | | |
| 121 | SEQ ID NO: 10 | | SEQ ID NO: 11 | SEQ ID NO: 12 | SEQ ID NO: 13 | |
| 122 | SEQ ID NO: 10 | | SEQ ID NO: 11 | SEQ ID NO: 12 | SEQ ID NO: 13 | SEQ ID NO: 14 |
| 123 | SEQ ID NO: 10 | | SEQ ID NO: 11 | | SEQ ID NO: 13 | |
| 124 | SEQ ID NO: 10 | | SEQ ID NO: 11 | | SEQ ID NO: 13 | SEQ ID NO: 14 |
| 125 | SEQ ID NO: 10 | | SEQ ID NO: 11 | | | SEQ ID NO: 14 |
| 126 | SEQ ID NO: 10 | | SEQ ID NO: 11 | SEQ ID NO: 12 | | SEQ ID NO: 14 |
| 127 | SEQ ID NO: 17 | | | | | |
| 128 | SEQ ID NO: 17 | KVS | | | | |
| 129 | SEQ ID NO: 17 | KVS | SEQ ID NO: 18 | | | |
| 130 | | KVS | | | | |
| 131 | | KVS | SEQ ID NO: 18 | | | |
| 132 | | | SEQ ID NO: 18 | | | |
| 133 | SEQ ID NO: 17 | | SEQ ID NO: 18 | | | |
| 134 | | | | SEQ ID NO: 19 | | |
| 135 | | | | SEQ ID NO: 19 | SEQ ID NO: 20 | |
| 136 | | | | SEQ ID NO: 19 | SEQ ID NO: 20 | SEQ ID NO: 21 |
| 137 | | | | | SEQ ID NO: 20 | |
| 138 | | | | | SEQ ID NO: 20 | SEQ ID NO: 21 |
| 139 | | | | | | SEQ ID NO: 21 |
| 140 | | | | SEQ ID NO: 19 | | SEQ ID NO: 21 |
| 141 | SEQ ID NO: 17 | | | SEQ ID NO: 19 | | |
| 142 | SEQ ID NO: 17 | | | SEQ ID NO: 19 | SEQ ID NO: 20 | |
| 143 | SEQ ID NO: 17 | | | SEQ ID NO: 19 | SEQ ID NO: 20 | SEQ ID NO: 21 |
| 144 | SEQ ID NO: 17 | | | | SEQ ID NO: 20 | |
| 145 | SEQ ID NO: 17 | | | | SEQ ID NO: 20 | SEQ ID NO: 21 |
| 146 | SEQ ID NO: 17 | | | | | SEQ ID NO: 21 |
| 147 | SEQ ID NO: 17 | | | SEQ ID NO: 19 | | SEQ ID NO: 21 |
| 148 | SEQ ID NO: 17 | KVS | | SEQ ID NO: 19 | | |
| 149 | SEQ ID NO: 17 | KVS | | SEQ ID NO: 19 | SEQ ID NO: 20 | |
| 150 | SEQ ID NO: 17 | KVS | | SEQ ID NO: 19 | SEQ ID NO: 20 | SEQ ID NO: 21 |
| 151 | SEQ ID NO: 17 | KVS | | | SEQ ID NO: 20 | |
| 152 | SEQ ID NO: 17 | KVS | | | SEQ ID NO: 20 | SEQ ID NO: 21 |
| 153 | SEQ ID NO: 17 | KVS | | | | SEQ ID NO: 21 |
| 154 | SEQ ID NO: 17 | KVS | | SEQ ID NO: 19 | | SEQ ID NO: 21 |
| 155 | SEQ ID NO: 17 | KVS | SEQ ID NO: 18 | SEQ ID NO: 19 | | |
| 156 | SEQ ID NO: 17 | KVS | SEQ ID NO: 18 | SEQ ID NO: 19 | SEQ ID NO: 20 | |

TABLE A-continued

| | Light Chain HVR | | | Heavy Chain HVR | | |
|---|---|---|---|---|---|---|
| Antibody | L1 | L2 | L3 | H1 | H2 | H3 |
| 157 | SEQ ID NO: 17 | KVS | SEQ ID NO: 18 | SEQ ID NO: 19 | SEQ ID NO: 20 | SEQ ID NO: 21 |
| 158 | SEQ ID NO: 17 | KVS | SEQ ID NO: 18 | | SEQ ID NO: 20 | |
| 159 | SEQ ID NO: 17 | KVS | SEQ ID NO: 18 | | SEQ ID NO: 20 | SEQ ID NO: 21 |
| 160 | SEQ ID NO: 17 | KVS | SEQ ID NO: 18 | SEQ ID NO: 19 | | SEQ ID NO: 21 |
| 161 | SEQ ID NO: 17 | KVS | SEQ ID NO: 18 | | | SEQ ID NO: 21 |
| 162 | | KVS | | SEQ ID NO: 19 | | |
| 163 | | KVS | | SEQ ID NO: 19 | SEQ ID NO: 20 | |
| 164 | | KVS | | SEQ ID NO: 19 | SEQ ID NO: 20 | SEQ ID NO: 21 |
| 165 | | KVS | | | SEQ ID NO: 20 | |
| 166 | | KVS | | | SEQ ID NO: 20 | SEQ ID NO: 21 |
| 167 | | KVS | | | | SEQ ID NO: 21 |
| 168 | | KVS | | SEQ ID NO: 19 | | SEQ ID NO: 21 |
| 169 | | KVS | SEQ ID NO: 18 | SEQ ID NO: 19 | | |
| 170 | | KVS | SEQ ID NO: 18 | SEQ ID NO: 19 | SEQ ID NO: 20 | |
| 171 | | KVS | SEQ ID NO: 18 | SEQ ID NO: 19 | SEQ ID NO: 20 | SEQ ID NO: 21 |
| 172 | | KVS | SEQ ID NO: 18 | | SEQ ID NO: 20 | |
| 173 | | KVS | SEQ ID NO: 18 | | SEQ ID NO: 20 | SEQ ID NO: 21 |
| 174 | | KVS | SEQ ID NO: 18 | | | SEQ ID NO: 21 |
| 175 | | KVS | SEQ ID NO: 18 | SEQ ID NO: 19 | | SEQ ID NO: 21 |
| 176 | | | SEQ ID NO: 18 | SEQ ID NO: 19 | | |
| 177 | | | SEQ ID NO: 18 | SEQ ID NO: 19 | SEQ ID NO: 20 | |
| 178 | | | SEQ ID NO: 18 | SEQ ID NO: 19 | SEQ ID NO: 20 | SEQ ID NO: 21 |
| 179 | | | SEQ ID NO: 18 | | SEQ ID NO: 20 | |
| 180 | | | SEQ ID NO: 18 | | SEQ ID NO: 20 | SEQ ID NO: 21 |
| 181 | | | SEQ ID NO: 18 | | | SEQ ID NO: 21 |
| 182 | | | SEQ ID NO: 18 | SEQ ID NO: 19 | | SEQ ID NO: 21 |
| 183 | SEQ ID NO: 17 | | SEQ ID NO: 18 | SEQ ID NO: 19 | | |
| 184 | SEQ ID NO: 17 | | SEQ ID NO: 18 | SEQ ID NO: 19 | SEQ ID NO: 20 | |
| 185 | SEQ ID NO: 17 | | SEQ ID NO: 18 | SEQ ID NO: 19 | SEQ ID NO: 20 | SEQ ID NO: 21 |
| 186 | SEQ ID NO: 17 | | SEQ ID NO: 18 | | SEQ ID NO: 20 | |
| 187 | SEQ ID NO: 17 | | SEQ ID NO: 18 | | SEQ ID NO: 20 | SEQ ID NO: 21 |
| 188 | SEQ ID NO: 17 | | SEQ ID NO: 18 | | | SEQ ID NO: 21 |
| 189 | SEQ ID NO: 17 | | SEQ ID NO: 18 | SEQ ID NO: 19 | | SEQ ID NO: 21 |
| 190 | SEQ ID NO: 24 | | | | | |
| 191 | SEQ ID NO: 24 | KVS | | | | |
| 192 | SEQ ID NO: 24 | KVS | SEQ ID NO: 25 | | | |
| 193 | | KVS | | | | |
| 194 | | KVS | SEQ ID NO: 25 | | | |
| 195 | | | SEQ ID NO: 25 | | | |
| 196 | SEQ ID NO: 24 | | SEQ ID NO: 25 | | | |
| 197 | | | | SEQ ID NO: 26 | | |
| 198 | | | | SEQ ID NO: 26 | SEQ ID NO: 27 | |
| 199 | | | | SEQ ID NO: 26 | SEQ ID NO: 27 | SEQ ID NO: 28 |
| 200 | | | | | SEQ ID NO: 27 | |
| 201 | | | | | SEQ ID NO: 27 | SEQ ID NO: 28 |
| 202 | | | | | | SEQ ID NO: 28 |
| 203 | | | | SEQ ID NO: 26 | | SEQ ID NO: 28 |
| 204 | SEQ ID NO: 24 | | | SEQ ID NO: 26 | | |
| 205 | SEQ ID NO: 24 | | | SEQ ID NO: 26 | SEQ ID NO: 27 | |
| 206 | SEQ ID NO: 24 | | | SEQ ID NO: 26 | SEQ ID NO: 27 | SEQ ID NO: 28 |
| 207 | SEQ ID NO: 24 | | | | SEQ ID NO: 27 | |
| 208 | SEQ ID NO: 24 | | | | SEQ ID NO: 27 | SEQ ID NO: 28 |
| 209 | SEQ ID NO: 24 | | | | | SEQ ID NO: 28 |
| 210 | SEQ ID NO: 24 | | | SEQ ID NO: 26 | | SEQ ID NO: 28 |
| 211 | SEQ ID NO: 24 | KVS | | SEQ ID NO: 26 | | |
| 212 | SEQ ID NO: 24 | KVS | | SEQ ID NO: 26 | SEQ ID NO: 27 | |
| 213 | SEQ ID NO: 24 | KVS | | SEQ ID NO: 26 | SEQ ID NO: 27 | SEQ ID NO: 28 |
| 214 | SEQ ID NO: 24 | KVS | | | SEQ ID NO: 27 | |
| 215 | SEQ ID NO: 24 | KVS | | | SEQ ID NO: 27 | SEQ ID NO: 28 |
| 216 | SEQ ID NO: 24 | KVS | | | | SEQ ID NO: 28 |
| 217 | SEQ ID NO: 24 | KVS | | SEQ ID NO: 26 | | SEQ ID NO: 28 |
| 218 | SEQ ID NO: 24 | KVS | SEQ ID NO: 25 | SEQ ID NO: 26 | | |
| 219 | SEQ ID NO: 24 | KVS | SEQ ID NO: 25 | SEQ ID NO: 26 | SEQ ID NO: 27 | |
| 220 | SEQ ID NO: 24 | KVS | SEQ ID NO: 25 | SEQ ID NO: 26 | SEQ ID NO: 27 | SEQ ID NO: 28 |
| 221 | SEQ ID NO: 24 | KVS | SEQ ID NO: 25 | | SEQ ID NO: 27 | |
| 222 | SEQ ID NO: 24 | KVS | SEQ ID NO: 25 | | SEQ ID NO: 27 | SEQ ID NO: 28 |
| 223 | SEQ ID NO: 24 | KVS | SEQ ID NO: 25 | SEQ ID NO: 26 | | SEQ ID NO: 28 |
| 224 | SEQ ID NO: 24 | KVS | SEQ ID NO: 25 | | | SEQ ID NO: 28 |
| 225 | | KVS | | SEQ ID NO: 26 | | |
| 226 | | KVS | | SEQ ID NO: 26 | SEQ ID NO: 27 | |
| 227 | | KVS | | SEQ ID NO: 26 | SEQ ID NO: 27 | SEQ ID NO: 28 |
| 228 | | KVS | | | SEQ ID NO: 27 | |
| 229 | | KVS | | | SEQ ID NO: 27 | SEQ ID NO: 28 |
| 230 | | KVS | | | | SEQ ID NO: 28 |
| 231 | | KVS | | SEQ ID NO: 26 | | SEQ ID NO: 28 |
| 232 | | KVS | SEQ ID NO: 25 | SEQ ID NO: 26 | | |

TABLE A-continued

| | Light Chain HVR | | | Heavy Chain HVR | | |
|---|---|---|---|---|---|---|
| Antibody | L1 | L2 | L3 | H1 | H2 | H3 |
| 233 | | KVS | SEQ ID NO: 25 | SEQ ID NO: 26 | SEQ ID NO: 27 | |
| 234 | | KVS | SEQ ID NO: 25 | SEQ ID NO: 26 | SEQ ID NO: 27 | SEQ ID NO: 28 |
| 235 | | KVS | SEQ ID NO: 25 | | SEQ ID NO: 27 | |
| 236 | | KVS | SEQ ID NO: 25 | | SEQ ID NO: 27 | SEQ ID NO: 28 |
| 237 | | KVS | SEQ ID NO: 25 | | | SEQ ID NO: 28 |
| 238 | | KVS | SEQ ID NO: 25 | SEQ ID NO: 26 | | SEQ ID NO: 28 |
| 239 | | | SEQ ID NO: 25 | SEQ ID NO: 26 | | |
| 240 | | | SEQ ID NO: 25 | SEQ ID NO: 26 | SEQ ID NO: 27 | |
| 241 | | | SEQ ID NO: 25 | SEQ ID NO: 26 | SEQ ID NO: 27 | SEQ ID NO: 28 |
| 242 | | | SEQ ID NO: 25 | | SEQ ID NO: 27 | |
| 243 | | | SEQ ID NO: 25 | | SEQ ID NO: 27 | SEQ ID NO: 28 |
| 244 | | | SEQ ID NO: 25 | | | SEQ ID NO: 28 |
| 245 | | | SEQ ID NO: 25 | SEQ ID NO: 26 | | SEQ ID NO: 28 |
| 246 | SEQ ID NO: 24 | | SEQ ID NO: 25 | SEQ ID NO: 26 | | |
| 247 | SEQ ID NO: 24 | | SEQ ID NO: 25 | SEQ ID NO: 26 | SEQ ID NO: 27 | |
| 248 | SEQ ID NO: 24 | | SEQ ID NO: 25 | SEQ ID NO: 26 | SEQ ID NO: 27 | SEQ ID NO: 28 |
| 249 | SEQ ID NO: 24 | | SEQ ID NO: 25 | | SEQ ID NO: 27 | |
| 250 | SEQ ID NO: 24 | | SEQ ID NO: 25 | | SEQ ID NO: 27 | SEQ ID NO: 28 |
| 251 | SEQ ID NO: 24 | | SEQ ID NO: 25 | | | SEQ ID NO: 28 |
| 252 | SEQ ID NO: 24 | | SEQ ID NO: 25 | SEQ ID NO: 26 | | SEQ ID NO: 28 |
| 253 | SEQ ID NO: 31 | | | | | |
| 254 | SEQ ID NO: 31 | KVS | | | | |
| 255 | SEQ ID NO: 31 | KVS | SEQ ID NO: 32 | | | |
| 256 | | KVS | | | | |
| 257 | | KVS | SEQ ID NO: 32 | | | |
| 258 | | | SEQ ID NO: 32 | | | |
| 259 | SEQ ID NO: 31 | | SEQ ID NO: 32 | | | |
| 260 | | | | SEQ ID NO: 33 | | |
| 261 | | | | SEQ ID NO: 33 | SEQ ID NO: 34 | |
| 262 | | | | SEQ ID NO: 33 | SEQ ID NO: 34 | SEQ ID NO: 35 |
| 263 | | | | | SEQ ID NO: 34 | |
| 264 | | | | | SEQ ID NO: 34 | SEQ ID NO: 35 |
| 265 | | | | | | SEQ ID NO: 35 |
| 266 | | | | SEQ ID NO: 33 | | SEQ ID NO: 35 |
| 267 | SEQ ID NO: 31 | | | SEQ ID NO: 33 | | |
| 268 | SEQ ID NO: 31 | | | SEQ ID NO: 33 | SEQ ID NO: 34 | |
| 269 | SEQ ID NO: 31 | | | SEQ ID NO: 33 | SEQ ID NO: 34 | SEQ ID NO: 35 |
| 270 | SEQ ID NO: 31 | | | | SEQ ID NO: 34 | |
| 271 | SEQ ID NO: 31 | | | | SEQ ID NO : 34 | SEQ ID NO: 35 |
| 272 | SEQ ID NO: 31 | | | | | SEQ ID NO: 35 |
| 273 | SEQ ID NO: 31 | | | SEQ ID NO: 33 | | SEQ ID NO: 35 |
| 274 | SEQ ID NO: 31 | KVS | | SEQ ID NO: 33 | | |
| 275 | SEQ ID NO: 31 | KVS | | SEQ ID NO: 33 | SEQ ID NO: 34 | |
| 276 | SEQ ID NO: 31 | KVS | | SEQ ID NO: 33 | SEQ ID NO: 34 | SEQ ID NO: 35 |
| 277 | SEQ ID NO: 31 | KVS | | | SEQ ID NO: 34 | |
| 278 | SEQ ID NO: 31 | KVS | | | SEQ ID NO: 34 | SEQ ID NO: 35 |
| 279 | SEQ ID NO: 31 | KVS | | | | SEQ ID NO: 35 |
| 280 | SEQ ID NO: 31 | KVS | | SEQ ID NO: 33 | | SEQ ID NO: 35 |
| 281 | SEQ ID NO: 31 | KVS | SEQ ID NO: 32 | SEQ ID NO: 33 | | |
| 282 | SEQ ID NO: 31 | KVS | SEQ ID NO: 32 | SEQ ID NO: 33 | SEQ ID NO: 34 | |
| 283 | SEQ ID NO: 31 | KVS | SEQ ID NO: 32 | SEQ ID NO: 33 | SEQ ID NO: 34 | SEQ ID NO: 35 |
| 284 | SEQ ID NO: 31 | KVS | SEQ ID NO: 32 | | SEQ ID NO: 34 | |
| 285 | SEQ ID NO: 31 | KVS | SEQ ID NO: 32 | | SEQ ID NO: 34 | SEQ ID NO: 35 |
| 286 | SEQ ID NO: 31 | KVS | SEQ ID NO: 32 | | | SEQ ID NO: 35 |
| 287 | SEQ ID NO: 31 | KVS | SEQ ID NO: 32 | SEQ ID NO: 33 | | SEQ ID NO: 35 |
| 288 | | KVS | | SEQ ID NO: 33 | | |
| 289 | | KVS | | SEQ ID NO: 33 | SEQ ID NO: 34 | |
| 290 | | KVS | | SEQ ID NO: 33 | SEQ ID NO: 34 | SEQ ID NO: 35 |
| 291 | | KVS | | | SEQ ID NO: 34 | |
| 292 | | KVS | | | SEQ ID NO: 34 | SEQ ID NO: 35 |
| 293 | | KVS | | | | SEQ ID NO: 35 |
| 294 | | KVS | | SEQ ID NO: 33 | | SEQ ID NO: 35 |
| 295 | | KVS | SEQ ID NO: 32 | SEQ ID NO: 33 | | |
| 296 | | KVS | SEQ ID NO: 32 | SEQ ID NO: 33 | SEQ ID NO: 34 | |
| 297 | | KVS | SEQ ID NO: 32 | SEQ ID NO: 33 | SEQ ID NO: 34 | SEQ ID NO: 35 |
| 298 | | KVS | SEQ ID NO: 32 | | SEQ ID NO: 34 | |
| 299 | | KVS | SEQ ID NO: 32 | | SEQ ID NO: 34 | SEQ ID NO: 35 |
| 300 | | KVS | SEQ ID NO: 32 | | | SEQ ID NO: 35 |
| 301 | | KVS | SEQ ID NO: 32 | SEQ ID NO: 33 | | SEQ ID NO: 35 |
| 302 | | | SEQ ID NO: 32 | SEQ ID NO: 33 | | |
| 303 | | | SEQ ID NO: 32 | SEQ ID NO: 33 | SEQ ID NO: 34 | |
| 304 | | | SEQ ID NO: 32 | SEQ ID NO: 33 | SEQ ID NO: 34 | SEQ ID NO: 35 |
| 305 | | | SEQ ID NO: 32 | | SEQ ID NO: 34 | |
| 306 | | | SEQ ID NO: 32 | | SEQ ID NO: 34 | SEQ ID NO: 35 |
| 307 | | | SEQ ID NO: 32 | | | SEQ ID NO: 35 |
| 308 | | | SEQ ID NO: 32 | SEQ ID NO: 33 | | SEQ ID NO: 35 |

TABLE A-continued

| Antibody | Light Chain HVR | | | Heavy Chain HVR | | |
| --- | --- | --- | --- | --- | --- | --- |
| | L1 | L2 | L3 | H1 | H2 | H3 |
| 309 | SEQ ID NO: 31 | | SEQ ID NO: 32 | SEQ ID NO: 33 | | |
| 310 | SEQ ID NO: 31 | | SEQ ID NO: 32 | SEQ ID NO: 33 | SEQ ID NO: 34 | |
| 311 | SEQ ID NO: 31 | | SEQ ID NO: 32 | SEQ ID NO: 33 | SEQ ID NO: 34 | SEQ ID NO: 35 |
| 312 | SEQ ID NO: 31 | | SEQ ID NO: 32 | | SEQ ID NO: 34 | |
| 313 | SEQ ID NO: 31 | | SEQ ID NO: 32 | | SEQ ID NO: 34 | SEQ ID NO: 35 |
| 314 | SEQ ID NO: 31 | | SEQ ID NO: 32 | | | SEQ ID NO: 35 |
| 315 | SEQ ID NO: 31 | | SEQ ID NO: 32 | SEQ ID NO: 33 | | SEQ ID NO: 35 |
| 316 | SEQ ID NO: 38 | | | | | |
| 317 | SEQ ID NO: 38 | WAS | | | | |
| 318 | SEQ ID NO: 38 | WAS | SEQ ID NO: 39 | | | |
| 319 | | WAS | | | | |
| 320 | | WAS | SEQ ID NO: 39 | | | |
| 321 | | | SEQ ID NO: 39 | | | |
| 322 | SEQ ID NO: 38 | | SEQ ID NO: 39 | | | |
| 323 | | | | SEQ ID NO: 40 | | |
| 324 | | | | SEQ ID NO: 40 | SEQ ID NO: 41 | |
| 325 | | | | SEQ ID NO: 40 | SEQ ID NO: 41 | SEQ ID NO: 42 |
| 326 | | | | | SEQ ID NO: 41 | |
| 327 | | | | | SEQ ID NO: 41 | SEQ ID NO: 42 |
| 328 | | | | | | SEQ ID NO: 42 |
| 329 | | | | SEQ ID NO: 40 | | SEQ ID NO: 42 |
| 330 | SEQ ID NO: 38 | | | SEQ ID NO: 40 | | |
| 331 | SEQ ID NO: 38 | | | SEQ ID NO: 40 | SEQ ID NO: 41 | |
| 332 | SEQ ID NO: 38 | | | SEQ ID NO: 40 | SEQ ID NO: 41 | SEQ ID NO: 42 |
| 333 | SEQ ID NO: 38 | | | | SEQ ID NO: 41 | |
| 334 | SEQ ID NO: 38 | | | | SEQ ID NO: 41 | SEQ ID NO: 42 |
| 335 | SEQ ID NO: 38 | | | | | SEQ ID NO: 42 |
| 336 | SEQ ID NO: 38 | | | SEQ ID NO: 40 | | SEQ ID NO: 42 |
| 337 | SEQ ID NO: 38 | WAS | | SEQ ID NO: 40 | | |
| 338 | SEQ ID NO: 38 | WAS | | SEQ ID NO: 40 | SEQ ID NO: 41 | |
| 339 | SEQ ID NO: 38 | WAS | | SEQ ID NO: 40 | SEQ ID NO: 41 | SEQ ID NO: 42 |
| 340 | SEQ ID NO: 38 | WAS | | | SEQ ID NO: 41 | |
| 341 | SEQ ID NO: 38 | WAS | | | SEQ ID NO: 41 | SEQ ID NO: 42 |
| 342 | SEQ ID NO: 38 | WAS | | | | SEQ ID NO: 42 |
| 343 | SEQ ID NO: 38 | WAS | | SEQ ID NO: 40 | | SEQ ID NO: 42 |
| 344 | SEQ ID NO: 38 | WAS | SEQ ID NO: 39 | SEQ ID NO: 40 | | |
| 345 | SEQ ID NO: 38 | WAS | SEQ ID NO: 39 | SEQ ID NO: 40 | SEQ ID NO: 41 | |
| 346 | SEQ ID NO: 38 | WAS | SEQ ID NO: 39 | SEQ ID NO: 40 | SEQ ID NO: 41 | SEQ ID NO: 42 |
| 347 | SEQ ID NO: 38 | WAS | SEQ ID NO: 39 | | SEQ ID NO: 41 | |
| 348 | SEQ ID NO: 38 | WAS | SEQ ID NO: 39 | | SEQ ID NO: 41 | SEQ ID NO: 42 |
| 349 | SEQ ID NO: 38 | WAS | SEQ ID NO: 39 | SEQ ID NO: 40 | | SEQ ID NO: 42 |
| 350 | SEQ ID NO: 38 | WAS | SEQ ID NO: 39 | | | SEQ ID NO: 42 |
| 351 | | WAS | | SEQ ID NO: 40 | | |
| 352 | | WAS | | SEQ ID NO: 40 | SEQ ID NO: 41 | |
| 353 | | WAS | | SEQ ID NO: 40 | SEQ ID NO: 41 | SEQ ID NO: 42 |
| 354 | | WAS | | | SEQ ID NO: 41 | |
| 355 | | WAS | | | SEQ ID NO: 41 | SEQ ID NO: 42 |
| 356 | | WAS | | | | SEQ ID NO: 42 |
| 357 | | WAS | | SEQ ID NO: 40 | | SEQ ID NO: 42 |
| 358 | | WAS | SEQ ID NO: 39 | SEQ ID NO: 40 | | |
| 359 | | WAS | SEQ ID NO: 39 | SEQ ID NO: 40 | SEQ ID NO: 41 | |
| 360 | | WAS | SEQ ID NO: 39 | SEQ ID NO: 40 | SEQ ID NO: 41 | SEQ ID NO: 42 |
| 361 | | WAS | SEQ ID NO: 39 | | SEQ ID NO: 41 | |
| 362 | | WAS | SEQ ID NO: 39 | | SEQ ID NO: 41 | SEQ ID NO: 42 |
| 363 | | WAS | SEQ ID NO: 39 | | | SEQ ID NO: 42 |
| 364 | | WAS | SEQ ID NO: 39 | SEQ ID NO: 40 | | SEQ ID NO: 42 |
| 365 | | | SEQ ID NO: 39 | SEQ ID NO: 40 | | |
| 366 | | | SEQ ID NO: 39 | SEQ ID NO: 40 | SEQ ID NO: 41 | |
| 367 | | | SEQ ID NO: 39 | SEQ ID NO: 40 | SEQ ID NO: 41 | SEQ ID NO: 42 |
| 368 | | | SEQ ID NO: 39 | | SEQ ID NO: 41 | |
| 369 | | | SEQ ID NO: 39 | | SEQ ID NO: 41 | SEQ ID NO: 42 |
| 370 | | | SEQ ID NO: 39 | | | SEQ ID NO: 42 |
| 371 | | | SEQ ID NO: 39 | SEQ ID NO: 40 | | SEQ ID NO: 42 |
| 372 | SEQ ID NO: 38 | | SEQ ID NO: 39 | SEQ ID NO: 40 | | |
| 373 | SEQ ID NO: 38 | | SEQ ID NO: 39 | SEQ ID NO: 40 | SEQ ID NO: 41 | |
| 374 | SEQ ID NO: 38 | | SEQ ID NO: 39 | SEQ ID NO: 40 | SEQ ID NO: 41 | SEQ ID NO: 42 |
| 375 | SEQ ID NO: 38 | | SEQ ID NO: 39 | | SEQ ID NO: 41 | |
| 376 | SEQ ID NO: 38 | | SEQ ID NO: 39 | | SEQ ID NO: 41 | SEQ ID NO: 42 |
| 377 | SEQ ID NO: 38 | | SEQ ID NO: 39 | | | SEQ ID NO: 42 |
| 378 | SEQ ID NO: 38 | | SEQ ID NO: 39 | SEQ ID NO: 40 | | SEQ ID NO: 42 |

In another example, an anti-ApoE antibody has a light chain variable region comprising a consensus sequence of SEQ ID NO: 45. The light chain variable region can further comprise a consensus sequence of SEQ ID NO: 44 and/or a consensus sequence of comprising the amino acid sequence (I/K)VS. In exemplary embodiments, SEQ ID NO: 44, 45, and 46 are L1, L2 and L3, respectively (e.g. antibodies 1-7 in Table B).

In some embodiments, the anti-TREM-2 antibody may further comprise a VH that has one or more HVRs derived from SEQ ID NO: 2. The HVR derived from SEQ ID NO: 2 may be H1, H2, H3, or any combination thereof. In certain embodiments, the VH may comprise an H1 of SEQ ID NO: 5, an H2 of SEQ ID NO: 6, an H3 of SEQ ID NO: 7, or any combination thereof (e.g. antibodies 8-56 in Table B).

In some embodiments, the anti-TREM-2 antibody may further comprise a VH that has one or more HVRs derived from SEQ ID NO: 9. The HVR derived from SEQ ID NO: 9 may be H1, H2, H3, or any combination thereof. In certain embodiments, the VH may comprise an H1 of SEQ ID NO: 12, an H2 of SEQ ID NO: 13, an H3 of SEQ ID NO: 14, or any combination thereof (e.g. antibodies 57-105 in Table B).

In some embodiments, the anti-TREM-2 antibody may further comprise a VH that has one or more HVRs derived from SEQ ID NO: 16. The HVR derived from SEQ ID NO: 16 may be H1, H2, H3, or any combination thereof. In certain embodiments, the VH may comprise an H1 of SEQ ID NO: 19, an H2 of SEQ ID NO: 20, an H3 of SEQ ID NO: 21, or any combination thereof (e.g. antibodies 106-154 in Table B).

In some embodiments, the anti-TREM-2 antibody may further comprise a VH that has one or more HVRs derived from SEQ ID NO: 23. The HVR derived from SEQ ID NO: 23 may be H1, H2, H3, or any combination thereof. In certain embodiments, the VH may comprise an H1 of SEQ ID NO: 26, an H2 of SEQ ID NO: 27, an H3 of SEQ ID NO: 28, or any combination thereof (e.g. antibodies 155-203 in Table B).

In some embodiments, the anti-TREM-2 antibody may further comprise a VH that has one or more HVRs derived from SEQ ID NO: 30. The HVR derived from SEQ ID NO: 30 may be H1, H2, H3, or any combination thereof. In certain embodiments, the VH may comprise an H1 of SEQ ID NO: 33, an H2 of SEQ ID NO: 34, an H3 comprising the amino acid sequence (I/K)VS, or any combination thereof (e.g. antibodies 204-252 in Table B).

TABLE B

| Antibody | Light Chain HVR | | | Heavy Chain HVR | | |
|---|---|---|---|---|---|---|
| | L1 | L2 | L3 | H1 | H2 | H3 |
| 1 | SEQ ID NO: 44 | | | | | |
| 2 | SEQ ID NO: 44 | (I/V)KS | | | | |
| 3 | SEQ ID NO: 44 | (I/V)KS | SEQ ID NO: 45 | | | |
| 4 | | (I/V)KS | | | | |
| 5 | | (I/V)KS | SEQ ID NO: 45 | | | |
| 6 | | | SEQ ID NO: 45 | | | |
| 7 | SEQ ID NO: 44 | | SEQ ID NO: 45 | | | |
| 8 | SEQ ID NO:50 | | | SEQ ID NO: 5 | | |
| 9 | SEQ ID NO: 44 | | | SEQ ID NO: 5 | SEQ ID NO: 6 | |
| 10 | SEQ ID NO: 44 | | | SEQ ID NO: 5 | SEQ ID NO: 6 | SEQ ID NO: 7 |
| 11 | SEQ ID NO: 44 | | | | SEQ ID NO: 6 | |
| 12 | SEQ ID NO: 44 | | | | SEQ ID NO: 6 | SEQ ID NO: 7 |
| 13 | SEQ ID NO: 44 | | | | | SEQ ID NO: 7 |
| 14 | SEQ ID NO: 44 | | | SEQ ID NO: 5 | | SEQ ID NO: 7 |
| 15 | SEQ ID NO: 44 | (I/V)KS | | SEQ ID NO: 5 | | |
| 16 | SEQ ID NO: 44 | (I/V)KS | | SEQ ID NO: 5 | SEQ ID NO: 6 | |
| 17 | SEQ ID NO: 44 | (I/V)KS | | SEQ ID NO: 5 | SEQ ID NO: 6 | SEQ ID NO: 7 |
| 18 | SEQ ID NO: 44 | (I/V)KS | | | SEQ ID NO: 6 | |
| 19 | SEQ ID NO: 44 | (I/V)KS | | | SEQ ID NO: 6 | SEQ ID NO: 7 |
| 20 | SEQ ID NO: 44 | (I/V)KS | | | | SEQ ID NO: 7 |
| 21 | SEQ ID NO: 44 | (I/V)KS | | SEQ ID NO: 5 | | SEQ ID NO: 7 |
| 22 | SEQ ID NO: 44 | (I/V)KS | SEQ ID NO: 45 | SEQ ID NO: 5 | | |
| 23 | SEQ ID NO: 44 | (I/V)KS | SEQ ID NO: 45 | SEQ ID NO: 5 | SEQ ID NO: 6 | |
| 24 | SEQ ID NO: 44 | (I/V)KS | SEQ ID NO: 45 | SEQ ID NO: 5 | SEQ ID NO: 6 | SEQ ID NO: 7 |
| 25 | SEQ ID NO: 44 | (I/V)KS | SEQ ID NO: 45 | | SEQ ID NO: 6 | |
| 26 | SEQ ID NO: 44 | (I/V)KS | SEQ ID NO: 45 | | SEQ ID NO: 6 | SEQ ID NO: 7 |
| 27 | SEQ ID NO: 44 | (I/V)KS | SEQ ID NO: 45 | SEQ ID NO: 5 | | SEQ ID NO: 7 |
| 28 | SEQ ID NO: 44 | (I/V)KS | SEQ ID NO: 45 | | | SEQ ID NO: 7 |
| 29 | | (I/V)KS | | SEQ ID NO: 5 | | |
| 30 | | (I/V)KS | | SEQ ID NO: 5 | SEQ ID NO: 6 | |
| 31 | | (I/V)KS | | SEQ ID NO: 5 | SEQ ID NO: 6 | SEQ ID NO: 7 |
| 32 | | (I/V)KS | | | SEQ ID NO: 6 | |
| 33 | | (I/V)KS | | | SEQ ID NO: 6 | SEQ ID NO: 7 |
| 34 | | (I/V)KS | | | | SEQ ID NO: 7 |
| 35 | | (I/V)KS | | SEQ ID NO: 5 | | SEQ ID NO: 7 |
| 36 | | (I/V)KS | SEQ ID NO: 45 | SEQ ID NO: 5 | | |
| 37 | | (I/V)KS | SEQ ID NO: 45 | SEQ ID NO: 5 | SEQ ID NO: 6 | |
| 38 | | (I/V)KS | SEQ ID NO: 45 | SEQ ID NO: 5 | SEQ ID NO: 6 | SEQ ID NO: 7 |
| 39 | | (I/V)KS | SEQ ID NO: 45 | | SEQ ID NO: 6 | |
| 40 | | (I/V)KS | SEQ ID NO: 45 | | SEQ ID NO: 6 | SEQ ID NO: 7 |
| 41 | | (I/V)KS | SEQ ID NO: 45 | | | SEQ ID NO: 7 |
| 42 | | (I/V)KS | SEQ ID NO: 45 | SEQ ID NO: 5 | | SEQ ID NO: 7 |
| 43 | | | SEQ ID NO: 45 | SEQ ID NO: 5 | | |
| 44 | | | SEQ ID NO: 45 | SEQ ID NO: 5 | SEQ ID NO: 6 | |
| 45 | | | SEQ ID NO: 45 | SEQ ID NO: 5 | SEQ ID NO: 6 | SEQ ID NO: 7 |
| 46 | | | SEQ ID NO: 45 | | SEQ ID NO: 6 | |

TABLE B-continued

| | Light Chain HVR | | | Heavy Chain HVR | | |
|---|---|---|---|---|---|---|
| Antibody | L1 | L2 | L3 | H1 | H2 | H3 |
| 47 | | | SEQ ID NO: 45 | | SEQ ID NO: 6 | SEQ ID NO: 7 |
| 48 | | | SEQ ID NO: 45 | | | SEQ ID NO: 7 |
| 49 | | | SEQ ID NO: 45 | SEQ ID NO: 5 | | SEQ ID NO: 7 |
| 50 | SEQ ID NO: 44 | | SEQ ID NO: 45 | SEQ ID NO: 5 | | |
| 51 | SEQ ID NO: 44 | | SEQ ID NO: 45 | SEQ ID NO: 5 | SEQ ID NO: 6 | |
| 52 | SEQ ID NO: 44 | | SEQ ID NO: 45 | SEQ ID NO: 5 | SEQ ID NO: 6 | SEQ ID NO: 7 |
| 53 | SEQ ID NO: 44 | | SEQ ID NO: 45 | | SEQ ID NO: 6 | |
| 54 | SEQ ID NO: 44 | | SEQ ID NO: 45 | | SEQ ID NO: 6 | SEQ ID NO: 7 |
| 55 | SEQ ID NO: 44 | | SEQ ID NO: 45 | | | SEQ ID NO: 7 |
| 56 | SEQ ID NO: 44 | | SEQ ID NO: 45 | SEQ ID NO: 5 | | SEQ ID NO: 7 |
| 57 | SEQ ID NO:50 | | | SEQ ID NO: 12 | | |
| 58 | SEQ ID NO: 44 | | | SEQ ID NO: 12 | SEQ ID NO: 13 | |
| 59 | SEQ ID NO: 44 | | | SEQ ID NO: 12 | SEQ ID NO: 13 | SEQ ID NO: 14 |
| 60 | SEQ ID NO: 44 | | | | SEQ ID NO: 13 | |
| 61 | SEQ ID NO: 44 | | | | SEQ ID NO: 13 | SEQ ID NO: 14 |
| 62 | SEQ ID NO: 44 | | | | | SEQ ID NO: 14 |
| 63 | SEQ ID NO: 44 | | | SEQ ID NO: 12 | | SEQ ID NO: 14 |
| 64 | SEQ ID NO: 44 (I/V)KS | | | SEQ ID NO: 12 | | |
| 65 | SEQ ID NO: 44 (I/V)KS | | | SEQ ID NO: 12 | SEQ ID NO: 13 | |
| 66 | SEQ ID NO: 44 (I/V)KS | | | SEQ ID NO: 12 | SEQ ID NO: 13 | SEQ ID NO: 14 |
| 67 | SEQ ID NO: 44 (I/V)KS | | | | SEQ ID NO: 13 | |
| 68 | SEQ ID NO: 44 (I/V)KS | | | | SEQ ID NO: 13 | SEQ ID NO: 14 |
| 69 | SEQ ID NO: 44 (I/V)KS | | | | | SEQ ID NO: 14 |
| 70 | SEQ ID NO: 44 (I/V)KS | | | SEQ ID NO: 12 | | SEQ ID NO: 14 |
| 71 | SEQ ID NO: 44 (I/V)KS | | SEQ ID NO: 45 | SEQ ID NO: 12 | | |
| 72 | SEQ ID NO: 44 (I/V)KS | | SEQ ID NO: 45 | SEQ ID NO: 12 | SEQ ID NO: 13 | |
| 73 | SEQ ID NO: 44 (I/V)KS | | SEQ ID NO: 45 | SEQ ID NO: 12 | SEQ ID NO: 13 | SEQ ID NO: 14 |
| 74 | SEQ ID NO: 44 (I/V)KS | | SEQ ID NO: 45 | | SEQ ID NO: 13 | |
| 75 | SEQ ID NO: 44 (I/V)KS | | SEQ ID NO: 45 | | SEQ ID NO: 13 | SEQ ID NO: 14 |
| 76 | SEQ ID NO: 44 (I/V)KS | | SEQ ID NO: 45 | | | SEQ ID NO: 14 |
| 77 | SEQ ID NO: 44 (I/V)KS | | SEQ ID NO: 45 | SEQ ID NO: 12 | | SEQ ID NO: 14 |
| 78 | | (I/V)KS | | SEQ ID NO: 12 | | |
| 79 | | (I/V)KS | | SEQ ID NO: 12 | SEQ ID NO: 13 | |
| 80 | | (I/V)KS | | SEQ ID NO: 12 | SEQ ID NO: 13 | SEQ ID NO: 14 |
| 81 | | (I/V)KS | | | SEQ ID NO: 13 | |
| 82 | | (I/V)KS | | | SEQ ID NO: 13 | SEQ ID NO: 14 |
| 83 | | (I/V)KS | | | | SEQ ID NO: 14 |
| 84 | | (I/V)KS | | SEQ ID NO: 12 | | SEQ ID NO: 14 |
| 85 | | (I/V)KS | SEQ ID NO: 45 | SEQ ID NO: 12 | | |
| 86 | | (I/V)KS | SEQ ID NO: 45 | SEQ ID NO: 12 | SEQ ID NO: 13 | |
| 87 | | (I/V)KS | SEQ ID NO: 45 | SEQ ID NO: 12 | SEQ ID NO: 13 | SEQ ID NO: 14 |
| 88 | | (I/V)KS | SEQ ID NO: 45 | | SEQ ID NO: 13 | |
| 89 | | (I/V)KS | SEQ ID NO: 45 | | SEQ ID NO: 13 | SEQ ID NO: 14 |
| 90 | | (I/V)KS | SEQ ID NO: 45 | | | SEQ ID NO: 14 |
| 91 | | (I/V)KS | SEQ ID NO: 45 | SEQ ID NO: 12 | | SEQ ID NO: 14 |
| 92 | | | SEQ ID NO: 45 | SEQ ID NO: 12 | | |
| 93 | | | SEQ ID NO: 45 | SEQ ID NO: 12 | SEQ ID NO: 13 | |
| 94 | | | SEQ ID NO: 45 | SEQ ID NO: 12 | SEQ ID NO: 13 | SEQ ID NO: 14 |
| 95 | | | SEQ ID NO: 45 | | SEQ ID NO: 13 | |
| 96 | | | SEQ ID NO: 45 | | SEQ ID NO: 13 | SEQ ID NO: 14 |
| 97 | | | SEQ ID NO: 45 | | | SEQ ID NO: 14 |
| 98 | | | SEQ ID NO: 45 | SEQ ID NO: 12 | | SEQ ID NO: 14 |
| 99 | SEQ ID NO: 44 | | SEQ ID NO: 45 | SEQ ID NO: 12 | | |
| 100 | SEQ ID NO: 44 | | SEQ ID NO: 45 | SEQ ID NO: 12 | SEQ ID NO: 13 | |
| 101 | SEQ ID NO: 44 | | SEQ ID NO: 45 | SEQ ID NO: 12 | SEQ ID NO: 13 | SEQ ID NO: 14 |
| 102 | SEQ ID NO: 44 | | SEQ ID NO: 45 | | SEQ ID NO: 13 | |
| 103 | SEQ ID NO: 44 | | SEQ ID NO: 45 | | SEQ ID NO: 13 | SEQ ID NO: 14 |
| 104 | SEQ ID NO: 44 | | SEQ ID NO: 45 | | | SEQ ID NO: 14 |
| 105 | SEQ ID NO: 44 | | SEQ ID NO: 45 | SEQ ID NO: 12 | | SEQ ID NO: 14 |
| 106 | SEQ ID NO: 44 | | | SEQ ID NO: 19 | | |
| 107 | SEQ ID NO: 44 | | | SEQ ID NO: 19 | SEQ ID NO: 20 | |
| 108 | SEQ ID NO: 44 | | | SEQ ID NO: 19 | SEQ ID NO: 20 | SEQ ID NO: 21 |
| 109 | SEQ ID NO: 44 | | | | SEQ ID NO: 20 | |
| 110 | SEQ ID NO: 44 | | | | SEQ ID NO: 20 | SEQ ID NO: 21 |
| 111 | SEQ ID NO: 44 | | | | | SEQ ID NO: 21 |
| 112 | SEQ ID NO: 44 | | | SEQ ID NO: 19 | | SEQ ID NO: 21 |
| 113 | SEQ ID NO: 44 (I/V)KS | | | SEQ ID NO: 19 | | |
| 114 | SEQ ID NO: 44 (I/V)KS | | | SEQ ID NO: 19 | SEQ ID NO: 20 | |
| 115 | SEQ ID NO: 44 (I/V)KS | | | SEQ ID NO: 19 | SEQ ID NO: 20 | SEQ ID NO: 21 |
| 116 | SEQ ID NO: 44 (I/V)KS | | | | SEQ ID NO: 20 | |
| 117 | SEQ ID NO: 44 (I/V)KS | | | | SEQ ID NO: 20 | SEQ ID NO: 21 |
| 118 | SEQ ID NO: 44 (I/V)KS | | | | | SEQ ID NO: 21 |
| 119 | SEQ ID NO: 44 (I/V)KS | | | SEQ ID NO: 19 | | SEQ ID NO: 21 |
| 120 | SEQ ID NO: 44 (I/V)KS | | SEQ ID NO: 45 | SEQ ID NO: 19 | | |
| 121 | SEQ ID NO: 44 (I/V)KS | | SEQ ID NO: 45 | SEQ ID NO: 19 | SEQ ID NO: 20 | |
| 122 | SEQ ID NO: 44 (I/V)KS | | SEQ ID NO: 45 | SEQ ID NO: 19 | SEQ ID NO: 20 | SEQ ID NO: 21 |

TABLE B-continued

| | Light Chain HVR | | | Heavy Chain HVR | | |
|---|---|---|---|---|---|---|
| Antibody | L1 | L2 | L3 | H1 | H2 | H3 |
| 123 | SEQ ID NO: 44 | (I/V)KS | SEQ ID NO: 45 | | SEQ ID NO: 20 | |
| 124 | SEQ ID NO: 44 | (I/V)KS | SEQ ID NO: 45 | | SEQ ID NO: 20 | SEQ ID NO: 21 |
| 125 | SEQ ID NO: 44 | (I/V)KS | SEQ ID NO: 45 | SEQ ID NO: 19 | | SEQ ID NO: 21 |
| 126 | SEQ ID NO: 44 | (I/V)KS | SEQ ID NO: 45 | | | SEQ ID NO: 21 |
| 127 | | (I/V)KS | | SEQ ID NO: 19 | | |
| 128 | | (I/V)KS | | SEQ ID NO: 19 | SEQ ID NO: 20 | |
| 129 | | (I/V)KS | | SEQ ID NO: 19 | SEQ ID NO: 20 | SEQ ID NO: 21 |
| 130 | | (I/V)KS | | | SEQ ID NO: 20 | |
| 131 | | (I/V)KS | | | SEQ ID NO: 20 | SEQ ID NO: 21 |
| 132 | | (I/V)KS | | | | SEQ ID NO: 21 |
| 133 | | (I/V)KS | | SEQ ID NO: 19 | | SEQ ID NO: 21 |
| 134 | | (I/V)KS | SEQ ID NO: 45 | SEQ ID NO: 19 | | |
| 135 | | (I/V)KS | SEQ ID NO: 45 | SEQ ID NO: 19 | SEQ ID NO: 20 | |
| 136 | | (I/V)KS | SEQ ID NO: 45 | SEQ ID NO: 19 | SEQ ID NO: 20 | SEQ ID NO: 21 |
| 137 | | (I/V)KS | SEQ ID NO: 45 | | SEQ ID NO: 20 | |
| 138 | | (I/V)KS | SEQ ID NO: 45 | | SEQ ID NO: 20 | SEQ ID NO: 21 |
| 139 | | (I/V)KS | SEQ ID NO: 45 | | | SEQ ID NO: 21 |
| 140 | | (I/V)KS | SEQ ID NO: 45 | SEQ ID NO: 19 | | SEQ ID NO: 21 |
| 141 | | | SEQ ID NO: 45 | SEQ ID NO: 19 | | |
| 142 | | | SEQ ID NO: 45 | SEQ ID NO: 19 | SEQ ID NO: 20 | |
| 143 | | | SEQ ID NO: 45 | SEQ ID NO: 19 | SEQ ID NO: 20 | SEQ ID NO: 21 |
| 144 | | | SEQ ID NO: 45 | | SEQ ID NO: 20 | |
| 145 | | | SEQ ID NO: 45 | | SEQ ID NO: 20 | SEQ ID NO: 21 |
| 146 | | | SEQ ID NO: 45 | | | SEQ ID NO: 21 |
| 147 | | | SEQ ID NO: 45 | SEQ ID NO: 19 | | SEQ ID NO: 21 |
| 148 | SEQ ID NO: 44 | | SEQ ID NO: 45 | SEQ ID NO: 19 | | |
| 149 | SEQ ID NO: 44 | | SEQ ID NO: 45 | SEQ ID NO: 19 | SEQ ID NO: 20 | |
| 150 | SEQ ID NO: 44 | | SEQ ID NO: 45 | SEQ ID NO: 19 | SEQ ID NO: 20 | SEQ ID NO: 21 |
| 151 | SEQ ID NO: 44 | | SEQ ID NO: 45 | | SEQ ID NO: 20 | |
| 152 | SEQ ID NO: 44 | | SEQ ID NO: 45 | | SEQ ID NO: 20 | SEQ ID NO: 21 |
| 153 | SEQ ID NO: 44 | | SEQ ID NO: 45 | | | SEQ ID NO: 21 |
| 154 | SEQ ID NO: 44 | | SEQ ID NO: 45 | SEQ ID NO: 19 | | SEQ ID NO: 21 |
| 155 | SEQ ID NO:50 | | | SEQ ID NO: 26 | | |
| 156 | SEQ ID NO: 44 | | | SEQ ID NO: 26 | SEQ ID NO: 27 | |
| 157 | SEQ ID NO: 44 | | | SEQ ID NO: 26 | SEQ ID NO: 27 | SEQ ID NO: 28 |
| 158 | SEQ ID NO: 44 | | | | SEQ ID NO: 27 | |
| 159 | SEQ ID NO: 44 | | | | SEQ ID NO: 27 | SEQ ID NO: 28 |
| 160 | SEQ ID NO: 44 | | | | | SEQ ID NO: 28 |
| 161 | SEQ ID NO: 44 | | | SEQ ID NO: 26 | | SEQ ID NO: 28 |
| 162 | SEQ ID NO: 44 | (I/V)KS | | SEQ ID NO: 26 | | |
| 163 | SEQ ID NO: 44 | (I/V)KS | | SEQ ID NO: 26 | SEQ ID NO: 27 | |
| 164 | SEQ ID NO: 44 | (I/V)KS | | SEQ ID NO: 26 | SEQ ID NO: 27 | SEQ ID NO: 28 |
| 165 | SEQ ID NO: 44 | (I/V)KS | | | SEQ ID NO: 27 | |
| 166 | SEQ ID NO: 44 | (I/V)KS | | | SEQ ID NO: 27 | SEQ ID NO: 28 |
| 167 | SEQ ID NO: 44 | (I/V)KS | | | | SEQ ID NO: 28 |
| 168 | SEQ ID NO: 44 | (I/V)KS | | SEQ ID NO: 26 | | SEQ ID NO: 28 |
| 169 | SEQ ID NO: 44 | (I/V)KS | SEQ ID NO: 45 | SEQ ID NO: 26 | | |
| 170 | SEQ ID NO: 44 | (I/V)KS | SEQ ID NO: 45 | SEQ ID NO: 26 | SEQ ID NO: 27 | |
| 171 | SEQ ID NO: 44 | (I/V)KS | SEQ ID NO: 45 | SEQ ID NO: 26 | SEQ ID NO: 27 | SEQ ID NO: 28 |
| 172 | SEQ ID NO: 44 | (I/V)KS | SEQ ID NO: 45 | | SEQ ID NO: 27 | |
| 173 | SEQ ID NO: 44 | (I/V)KS | SEQ ID NO: 45 | | SEQ ID NO: 27 | SEQ ID NO: 28 |
| 174 | SEQ ID NO: 44 | (I/V)KS | SEQ ID NO: 45 | SEQ ID NO: 26 | | SEQ ID NO: 28 |
| 175 | SEQ ID NO: 44 | (I/V)KS | SEQ ID NO: 45 | | | SEQ ID NO: 28 |
| 176 | | (I/V)KS | | SEQ ID NO: 26 | | |
| 177 | | (I/V)KS | | SEQ ID NO: 26 | SEQ ID NO: 27 | |
| 178 | | (I/V)KS | | SEQ ID NO: 26 | SEQ ID NO: 27 | SEQ ID NO: 28 |
| 179 | | (I/V)KS | | | SEQ ID NO: 27 | |
| 180 | | (I/V)KS | | | SEQ ID NO: 27 | SEQ ID NO: 28 |
| 181 | | (I/V)KS | | | | SEQ ID NO: 28 |
| 182 | | (I/V)KS | | SEQ ID NO: 26 | | SEQ ID NO: 28 |
| 183 | | (I/V)KS | SEQ ID NO: 45 | SEQ ID NO: 26 | | |
| 184 | | (I/V)KS | SEQ ID NO: 45 | SEQ ID NO: 26 | SEQ ID NO: 27 | |
| 185 | | (I/V)KS | SEQ ID NO: 45 | SEQ ID NO: 26 | SEQ ID NO: 27 | SEQ ID NO: 28 |
| 186 | | (I/V)KS | SEQ ID NO: 45 | | SEQ ID NO: 27 | |
| 187 | | (I/V)KS | SEQ ID NO: 45 | | SEQ ID NO: 27 | SEQ ID NO: 28 |
| 188 | | (I/V)KS | SEQ ID NO: 45 | | | SEQ ID NO: 28 |
| 189 | | (I/V)KS | SEQ ID NO: 45 | SEQ ID NO: 26 | | SEQ ID NO: 28 |
| 190 | | | SEQ ID NO: 45 | SEQ ID NO: 26 | | |
| 191 | | | SEQ ID NO: 45 | SEQ ID NO: 26 | SEQ ID NO: 27 | |
| 192 | | | SEQ ID NO: 45 | SEQ ID NO: 26 | SEQ ID NO: 27 | SEQ ID NO: 28 |
| 193 | | | SEQ ID NO: 45 | | SEQ ID NO: 27 | |
| 194 | | | SEQ ID NO: 45 | | SEQ ID NO: 27 | SEQ ID NO: 28 |
| 195 | | | SEQ ID NO: 45 | | | SEQ ID NO: 28 |
| 196 | | | SEQ ID NO: 45 | SEQ ID NO: 26 | | SEQ ID NO: 28 |
| 197 | SEQ ID NO: 44 | | SEQ ID NO: 45 | SEQ ID NO: 26 | | |
| 198 | SEQ ID NO: 44 | | SEQ ID NO: 45 | SEQ ID NO: 26 | SEQ ID NO: 27 | |

TABLE B-continued

| | Light Chain HVR | | | Heavy Chain HVR | | |
|---|---|---|---|---|---|---|
| Antibody | L1 | L2 | L3 | H1 | H2 | H3 |
| 199 | SEQ ID NO: 44 | SEQ ID NO: 45 | SEQ ID NO: 26 | SEQ ID NO: 27 | SEQ ID NO: 28 | |
| 200 | SEQ ID NO: 44 | SEQ ID NO: 45 | | | SEQ ID NO: 27 | |
| 201 | SEQ ID NO: 44 | SEQ ID NO: 45 | | | SEQ ID NO: 27 | SEQ ID NO: 28 |
| 202 | SEQ ID NO: 44 | SEQ ID NO: 45 | | | | SEQ ID NO: 28 |
| 203 | SEQ ID NO: 44 | SEQ ID NO: 45 | SEQ ID NO: 26 | | | SEQ ID NO: 28 |
| 204 | SEQ ID NO:50 | | | SEQ ID NO: 33 | | |
| 205 | SEQ ID NO: 44 | | | SEQ ID NO: 33 | SEQ ID NO: 34 | |
| 206 | SEQ ID NO: 44 | | | SEQ ID NO: 33 | SEQ ID NO: 34 | SEQ ID NO: 35 |
| 207 | SEQ ID NO: 44 | | | | SEQ ID NO: 34 | |
| 208 | SEQ ID NO: 44 | | | | SEQ ID NO: 34 | SEQ ID NO: 35 |
| 209 | SEQ ID NO: 44 | | | | | SEQ ID NO: 35 |
| 210 | SEQ ID NO: 44 | | | SEQ ID NO: 33 | | SEQ ID NO: 35 |
| 211 | SEQ ID NO: 44 (I/V)KS | | | SEQ ID NO: 33 | | |
| 212 | SEQ ID NO: 44 (I/V)KS | | | SEQ ID NO: 33 | SEQ ID NO: 34 | |
| 213 | SEQ ID NO: 44 (I/V)KS | | | SEQ ID NO: 33 | SEQ ID NO: 34 | SEQ ID NO: 35 |
| 214 | SEQ ID NO: 44 (I/V)KS | | | | SEQ ID NO: 34 | |
| 215 | SEQ ID NO: 44 (I/V)KS | | | | SEQ ID NO: 34 | SEQ ID NO: 35 |
| 216 | SEQ ID NO: 44 (I/V)KS | | | | | SEQ ID NO: 35 |
| 217 | SEQ ID NO: 44 (I/V)KS | | | SEQ ID NO: 33 | | SEQ ID NO: 35 |
| 218 | SEQ ID NO: 44 (I/V)KS | SEQ ID NO: 45 | | SEQ ID NO: 33 | | |
| 219 | SEQ ID NO: 44 (I/V)KS | SEQ ID NO: 45 | | SEQ ID NO: 33 | SEQ ID NO: 34 | |
| 220 | SEQ ID NO: 44 (I/V)KS | SEQ ID NO: 45 | | SEQ ID NO: 33 | SEQ ID NO: 34 | SEQ ID NO: 35 |
| 221 | SEQ ID NO: 44 (I/V)KS | SEQ ID NO: 45 | | | SEQ ID NO: 34 | |
| 222 | SEQ ID NO: 44 (I/V)KS | SEQ ID NO: 45 | | | SEQ ID NO: 34 | SEQ ID NO: 35 |
| 223 | SEQ ID NO: 44 (I/V)KS | SEQ ID NO: 45 | | SEQ ID NO: 33 | | SEQ ID NO: 35 |
| 224 | SEQ ID NO: 44 (I/V)KS | SEQ ID NO: 45 | | | | SEQ ID NO: 35 |
| 225 | | (I/V)KS | | SEQ ID NO: 33 | | |
| 226 | | (I/V)KS | | SEQ ID NO: 33 | SEQ ID NO: 34 | |
| 227 | | (I/V)KS | | SEQ ID NO: 33 | SEQ ID NO: 34 | SEQ ID NO: 35 |
| 228 | | (I/V)KS | | | SEQ ID NO: 34 | |
| 229 | | (I/V)KS | | | SEQ ID NO: 34 | SEQ ID NO: 35 |
| 230 | | (I/V)KS | | | | SEQ ID NO: 35 |
| 231 | | (I/V)KS | | SEQ ID NO: 33 | | SEQ ID NO: 35 |
| 232 | | (I/V)KS | SEQ ID NO: 45 | SEQ ID NO: 33 | | |
| 233 | | (I/V)KS | SEQ ID NO: 45 | SEQ ID NO: 33 | SEQ ID NO: 34 | |
| 234 | | (I/V)KS | SEQ ID NO: 45 | SEQ ID NO: 33 | SEQ ID NO: 34 | SEQ ID NO: 35 |
| 235 | | (I/V)KS | SEQ ID NO: 45 | | SEQ ID NO: 34 | |
| 236 | | (I/V)KS | SEQ ID NO: 45 | | SEQ ID NO: 34 | SEQ ID NO: 35 |
| 237 | | (I/V)KS | SEQ ID NO: 45 | | | SEQ ID NO: 35 |
| 238 | | (I/V)KS | SEQ ID NO: 45 | SEQ ID NO: 33 | | SEQ ID NO: 35 |
| 239 | | | SEQ ID NO: 45 | SEQ ID NO: 33 | | |
| 240 | | | SEQ ID NO: 45 | SEQ ID NO: 33 | SEQ ID NO: 34 | |
| 241 | | | SEQ ID NO: 45 | SEQ ID NO: 33 | SEQ ID NO: 34 | SEQ ID NO: 35 |
| 242 | | | SEQ ID NO: 45 | | SEQ ID NO: 34 | |
| 243 | | | SEQ ID NO: 45 | | SEQ ID NO: 34 | SEQ ID NO: 35 |
| 244 | | | SEQ ID NO: 45 | | | SEQ ID NO: 35 |
| 245 | | | SEQ ID NO: 45 | SEQ ID NO: 33 | | SEQ ID NO: 35 |
| 246 | SEQ ID NO: 44 | | SEQ ID NO: 45 | SEQ ID NO: 33 | | |
| 247 | SEQ ID NO: 44 | | SEQ ID NO: 45 | SEQ ID NO: 33 | SEQ ID NO: 34 | |
| 248 | SEQ ID NO: 44 | | SEQ ID NO: 45 | SEQ ID NO: 33 | SEQ ID NO: 34 | SEQ ID NO: 35 |
| 249 | SEQ ID NO: 44 | | SEQ ID NO: 45 | | SEQ ID NO: 34 | |
| 250 | SEQ ID NO: 44 | | SEQ ID NO: 45 | | SEQ ID NO: 34 | SEQ ID NO: 35 |
| 251 | SEQ ID NO: 44 | | SEQ ID NO: 45 | | | SEQ ID NO: 35 |
| 252 | SEQ ID NO: 44 | | SEQ ID NO: 45 | SEQ ID NO: 33 | | SEQ ID NO: 35 |

In other examples, an anti-TREM-2 antibody of the present disclosure is HJ23.4. HJ23.7, HJ23.8, HJ23.9, HJ23.10, or HJ23.13. In still other examples, an anti-TREM-2 antibody of the present disclosure is a humanized antibody derived from HJ23.4, HJ23.7, HJ23.8, HJ23.9, HJ23.10, or HJ23.13.

In other examples, an anti-TREM-2 antibody of the present disclosure competitively inhibits binding of a reference antibody to its epitope. An antibody is said to competitively inhibit binding of a reference antibody to a given epitope if the antibody preferentially binds to that epitope to the extent that it blocks binding of the reference antibody to the epitope by at least 50%, at least 60%, at least 70%, at least 80%, or at least 90%. Competitive inhibition can be determined by any method known in the art, for example, competition ELISA assays. In some embodiments, an anti-TREM-2 antibody of the present disclosure competitively inhibits HJ23.4, HJ23.7, HJ23.8, HJ23.9, HJ23.10, or HJ23.13 binding to human TREM-2.

III. Treatment Methods

In another aspect, the present disclosure provides a method of increasing TREM-2 activation in a subject in need thereof. The method comprises administering a therapeutically effective amount of an anti-TREM-2 agonist antibody to a subject in need thereof. Suitable anti-TREM-2 agonist antibodies are described in Section II. In embodiments where the subject is a human, the anti-TREM-2 agonist antibody is adapted for administration to a living human subject (e.g. humanized). In various embodiments, an anti-TREM-2 agonist antibody is (a) an antibody selected from Table A, (b) an antibody selected from Table B, (c) is an anti-TREM-2 agonist antibody that competitively inhibits HJ23.4. HJ23.7, HJ23.8, HJ23.9. HJ23.10 or HJ23.13 binding to human TREM-2, (d) HJ23.4, HJ23.7, HJ23.8, HJ23.9, HJ23.10 or HJ23.13, or (e) a humanized derivative of HJ23.4, HJ23.7, HJ23.8, HJ23.9, HJ23.10 or HJ23.13.

Methods for evaluating TREM-2 activation are known in the art and include, but are not limited to, measuring an increase in an intracellular mediator or a signaling cascade activated by TREM-2. For example, TREM-2 activation may result in an increase in a TREM-2 activity selected from TREM-2 binding to DAP12; DAP12 binding to TREM-2; DAP12 phosphorylation; PI3K activation; increased expression of one or more anti-inflammatory mediators (e.g., cytokines) selected from the group consisting of IL-12p70, IL-6, and IL-10; reduced expression of one or more pro-inflammatory mediators selected from the group consisting of IFN-α4, IFN-b, IL-6, IL-12 p70, IL-1B, TNF, TNF-α, IL-10, IL-8, CRP, TGF-beta members of the chemokine protein families, IL-20 family members, IL-33, LIF, IFN-gamma, OSM, CNTF, TGF-beta, GM-CSF, IL-11, IL-12, IL-17, IL-18, and CRP; reduced expression of TNF-α, IL-6, or both; extracellular signal-regulated kinase (ERK) phosphorylation; increased expression of C—C chemokine receptor 7 (CCR7); induction of microglial cell chemotaxis toward CCL19 and CCL21 expressing cells; an increase, normalization, or both of the ability of bone marrow-derived dendritic cells to induce antigen-specific T-cell proliferation; induction of osteoclast production, increased rate of osteoclastogenesis, or both; increasing the survival and/or function of one or more of dendritic cells, macrophages, microglial cells, M1 macrophages and/or microglial cells, activated M1 macrophages and/or microglial cells, M2 macrophages and/or microglial cells, monocytes, osteoclasts, Langerhans cells of skin, and Kupffer cells; induction of one or more types of clearance selected from the group consisting of apoptotic neuron clearance, nerve tissue debris clearance, non-nerve tissue debris clearance, bacteria or other foreign body clearance, disease-causing protein clearance, disease-causing peptide clearance, and disease-causing nucleic acid clearance; induction of phagocytosis of one or more of apoptotic neurons, nerve tissue debris, non-nerve tissue debris, bacteria, other foreign bodies, disease-causing proteins, disease-causing peptides, or disease-causing nucleic acids; normalization of disrupted TREM-2/DAP12-dependent gene expression; recruitment of Syk, ZAP70, or both to the TREM-2/DAP12 complex; Syk phosphorylation; increased expression of CD83 and/or CD86 on dendritic cells, macrophages, monocytes, and/or microglia; reduced secretion of one or more inflammatory cytokines selected from the group consisting of TNF-α, IL-10, IL-6, MCP-1, IFN-α4, IFN-b, IL-1B, IL-8. CRP, TGF-beta members of the chemokine protein families, IL-20 family members, IL-33, LIF, IFN-gamma, OSM, CNTF, TGF-beta, GM-CSF, IL-11, IL-12, IL-17, IL-18, and CRP; reduced expression of one or more inflammatory receptors; increasing phagocytosis by macrophages, dendritic cells, monocytes, and/or microglia under conditions of reduced levels of MCSF; decreasing phagocytosis by macrophages, dendritic cells, monocytes, and/or microglia in the presence of normal levels of MCSF; increasing activity of one or more TREM-2-dependent genes; and any combination thereof.

In various embodiments, increasing TREM-2 activation induces or retains TREM-2 clustering on a cell surface. In other embodiments, increasing TREM-2 activation increases a TREM-2 activity selected from the group consisting of TREM-2 binding to DAP12; DAP12 phosphorylation; increasing the survival of macrophages, microglial cells, M1 microglial cells, activated M1 microglial cells, M2 microglial cells, dendritic cells, macrophages, M1 macrophages, activated M1 macrophages, M2 macrophages, monocytes, osteoclasts, Langerhans cells of skin, and/or Kupffer cells; increased expression of IL-6: Syk phosphorylation; increased expression of CD83 and/or CD86 on dendritic cells; increasing phagocytosis by macrophages, dendritic cells, monocytes, and/or microglia; and increasing activity of one or more TREM-2-dependent genes, optionally wherein the one or more TREM-2-dependent genes comprise one or more nuclear factor of activated T-cells (NFAT) transcription factors; and any combination thereof. In other embodiments, increasing TREM-2 activation induces or promotes innate immune cell survival.

Subjects in need of treatment include, but are not limited to, subjects with a disease, disorder, or injury selected from the group consisting of dementia, frontotemporal dementia, Alzheimer's disease, vascular dementia, mixed dementia, Creutzfeldt-Jakob disease, normal pressure hydrocephalus, amyotrophic lateral sclerosis, Huntington's disease, Tauopathy disease, Nasu-Hakola disease, stroke, acute trauma, chronic trauma, lupus, acute and chronic colitis, wound healing, Crohn's disease, inflammatory bowel disease, ulcerative colitis, obesity, Malaria, essential tremor, central nervous system lupus, Behcet's disease, Parkinson's disease, dementia with Lewy bodies, multiple system atrophy, Shy-Drager syndrome, progressive supranuclear palsy, cortical basal ganglionic degeneration, acute disseminated encephalomyelitis, granulomartous disorders, Sarcoidosis, diseases of aging, seizures, spinal cord injury, traumatic brain injury, age related macular degeneration, glaucoma, retinitis pigmentosa, retinal degeneration, respiratory tract infection, sepsis, eye infection, systemic infection, lupus, arthritis, multiple sclerosis, low bone density, osteoporosis, osteogenesis, osteopetrotic disease, Paget's disease of bone, and cancer, comprising administering to the individual a therapeutically effective amount of an isolated antibody of any one of the preceding embodiments. Other aspects of the present disclosure relate to an isolated antibody of any one of the preceding embodiments for use in preventing, reducing risk, or treating an individual having a disease, disorder, or injury selected from the group consisting of dementia, frontotemporal dementia, Alzheimer's disease, vascular dementia, mixed dementia, Creutzfeldt-Jakob disease, normal pressure hydrocephalus, amyotrophic lateral sclerosis, Huntington's disease, Taupathy disease, Nasu-Hakola disease, stroke, acute trauma, chronic trauma, lupus, acute and chronic colitis, wound healing, Crohn's disease, inflammatory bowel disease, ulcerative colitis, obesity, Malaria, essential tremor, central nervous system lupus, Behcet's disease, Parkinson's disease, dementia with Lewy bodies, multiple system atrophy, Shy-Drager syndrome, progressive supranuclear palsy, cortical basal ganglionic degeneration, acute disseminated encephalomyelitis, granulomartous disorders, Sarcoidosis, diseases of aging, seizures, spinal cord injury, traumatic brain injury, age related macular degeneration, glaucoma, retinitis pigmentosa, retinal degeneration, respiratory tract infection, sepsis, eye infection, systemic infection, lupus, arthritis, multiple sclerosis, low bone density, osteoporosis, osteogenesis, osteopetrotic disease, Paget's disease of bone, and cancer. Other aspects of the present disclosure relate to use of an isolated antibody of any one of the preceding embodiments in the manufacture of a medicament for preventing, reducing risk, or treating an individual having a disease, disorder, or injury selected from the group consisting of dementia, frontotemporal dementia.

Alzheimer's disease, vascular dementia, mixed dementia, Creutzfeldt-Jakob disease, normal pressure hydrocephalus, amyotrophic lateral sclerosis, Huntington's disease, Taupathy disease, Nasu-Hakola disease, stroke, acute trauma, chronic trauma, lupus, acute and chronic colitis, wound healing, Crohn's disease, inflammatory bowel disease, ulcerative colitis, obesity, Malaria, essential tremor, central nervous system lupus, Behcet's disease, Parkinson's disease, dementia with Lewy bodies, multiple system atrophy, Shy-Drager syndrome, progressive supranuclear palsy, cortical basal ganglionic degeneration, acute disseminated encephalomyelitis, granulomartous disorders, Sarcoidosis, diseases of aging, seizures, spinal cord injury, traumatic brain injury, age related macular degeneration, glaucoma, retinitis pigmentosa, retinal degeneration, respiratory tract infection, sepsis, eye infection, systemic infection, lupus, arthritis, multiple sclerosis, low bone density, osteoporosis, osteogenesis, osteopetrotic disease, Paget's disease of bone, and cancer. In various embodiments, the subject in need of treatment is a subject with a neurodegenerative disease. In certain embodiments, the subject with a neurodegenerative disease is a subject with Alzheimer's Disease (AD), frontotemporal dementia (FTD), amyotrophic lateral sclerosis (ALS), prion disease, Nasu-Hakola disease, and multiple sclerosis, or Parkinson's disease (PD), etc.). In other embodiments, the subject in need of treatment is a subject with that has had a stroke, or is at risk of developing a stroke. In other embodiments, the subject in need of treatment is a subject with acute or chronic pain.

In another aspect, the present disclosure provides a method of treating Aβ amyloidosis, the method comprising administering a therapeutically effective amount of an anti-TREM-2 agonist antibody to a subject in need thereof. The present disclosure also provides a method of treating a subject diagnosed with a disease characterized by brain Aβ plaques, the method comprising administering a therapeutically effective amount of an anti-TREM-2 agonist antibody to the subject. The present disclosure also provides a method of treating a subject diagnosed with a disease characterized by vascular Aβ plaques in the brain, the method comprising administering a therapeutically effective amount of an anti-TREM-2 agonist antibody to the subject. The present disclosure also provides a method of preventing the progression of a disease characterized by Aβ plaques in the brain, the method comprising administering a therapeutically effective amount of an anti-TREM-2 agonist antibody to a subject in need thereof. The present disclosure also provides a method of treating a subject diagnosed with Alzheimer's disease, the method comprising administering a therapeutically effective amount of an anti-TREM-2 agonist antibody to the subject. The present disclosure also provides a method of treating a subject diagnosed with CAA, the method comprising administering a therapeutically effective amount of an anti-TREM-2 agonist antibody to the subject. Suitable anti-TREM-2 agonist antibodies are described in Section II. In embodiments where the subject is a human, the anti-TREM-2 agonist antibody is adapted for administration to a living human subject (e.g. humanized).

In one embodiment, the disclosure provides a method of preventing the progression, or slowing the rate of progression, of a disease characterized by Aβ plaques in the brain. The method comprises administering a therapeutically effective amount of an anti-TREM-2 agonist antibody to a subject in need thereof. Suitable anti-TREM-2 agonist antibodies include those disclosed herein. Progression of a disease characterized by Aβ plaques in the brain can be evaluated by methods known in the art and described herein, including a worsening of a clinical sign of Aβ amyloidosis, onset or worsening of tau pathology, a worsening of an Aβ plaque associated symptom, or a worsening of a CAA associated symptom. In exemplary embodiments, the clinical sign is amyloid plaque load, tau pathology.

In another embodiment, the disclosure provides a method for improving a clinical sign of Aβ amyloidosis. The method comprises administering a therapeutically effective amount of an anti-TREM-2 agonist antibody to a subject in need thereof. Suitable anti-TREM-2 agonist antibodies include those disclosed herein. Non-limiting examples of improved clinical signs of Aβ amyloidosis may include a decrease in amyloid plaque load, stabilization of amyloid plaque load (i.e. no further increase), an increase in CSF Aβ42 concentration, an increase in CSF Aβ42/Aβ40 ratio, a decreased Aβ42/Aβ40 peak time ratio as measured by stable isotope labeling kinetics (e.g. such that is closer to 1), a decreased Aβ42/Aβ40 FTR ratio as measured by stable isotope labeling kinetics (e.g. such that is closer to 1), and a change in the ratio of the relative labeling Aβ42 to the relative labeling of Aβ40 (or another Aβ peptide) after stable isotope labeling such that the ratio is closer to 1. In each of the above embodiments, the improvement (i.e. the change) in the clinical sign is at least statistically significant. In certain embodiments, the change may be at least 1, 2, 3, 4, 5, 6, 7, 8, 9, 10, 11, 12, 13, 14, 15, 16, 17, 18, 19, or 20% compared to untreated or negative control treated subjects. In some embodiments, the change may be at least 20, 25, 30, 35, 40, 45, 50, 55, 60, 65, 70, 75, 80, 85, 90, or 95% compared to untreated or negative control treated subjects. In other embodiments, the change may be at least 100, 125, 150, 200, 250, 300, 350, 400, or 450% compared to untreated or negative control treated subjects.

In another embodiment, the disclosure provides a method for decreasing amyloid plaque load in the brain of a subject. The method comprises administering a therapeutically effective amount of an anti-TREM-2 agonist antibody to a subject. Suitable anti-TREM-2 agonist antibodies include those disclosed herein. A method of the invention may decrease the amyloid plaque load in the hippocampus of a subject and/or decrease the amyloid plaque load in the brain cortex of a subject. In each of the above embodiments, the amyloid plaque load may be decreased by at least 1, 2, 3, 4, 5, 6, 7, 8, 9, 10, 11, 12, 13, 14, 15, 16, 17, 18, 19, or 20% compared to untreated or negative control treated subjects. In some embodiments, the amyloid plaque load may be decreased by at least 20, 25, 30, 35, 40, 45, 50, 55, 60, 65, 70, 75, 80, 85, 90, or 95% compared to untreated or negative control treated subjects. In other embodiments, the amyloid plaque load may be decreased by at least 100, 125, 150, 200, 250, 300, 350, 400, or 450% compared to untreated or negative control treated subjects.

In another embodiment, the disclosure provides a method for decreasing CAA load in the brain of a subject. The method comprises administering a therapeutically effective amount of an anti-TREM-2 agonist antibody to a subject with fibrillar forms of Aβ in penetrating and/or leptomeningeal arterioles on the surface of the cerebral cortex. Suitable anti-TREM-2 agonist antibodies include those disclosed herein. A method of the invention may decrease CAA load in the penetrating and/or leptomeningeal arterioles on the surface of the cerebral cortex of a subject. In each of the above embodiments, CAA load may be decreased by at least 1, 2, 3, 4, 5, 6, 7, 8, 9, 10, 11, 12, 13, 14, 15, 16, 17, 18, 19, or 20% compared to untreated or negative control treated subjects. In some embodiments, the amyloid plaque load may be decreased by at least 20, 25, 30, 35, 40, 45, 50, 55, 60, 65, 70, 75, 80, 85, 90, or 95% compared to untreated or negative control treated subjects. In other embodiments, the amyloid plaque load may be decreased by at least 100, 125, 150, 200, 250, 300, 350, 400, or 450% compared to untreated or negative control treated subjects.

Another embodiment includes a method of reducing insoluble Aβ42 levels in the brain of a subject in need thereof. The method comprises administering a therapeutically effective amount of an anti-TREM-2 agonist antibody to the subject. In one example, the method further comprises reducing insoluble Aβ40 levels in the brain of the subject. In another example, the method comprises selectively reducing insoluble Aβ40 levels, reducing insoluble Aβ42 levels, or a combination thereof compared to soluble Aβ40, Aβ42 levels, or a combination thereof in the brain of a subject.

The level of Aβ can be assessed by any suitable method known in the art comprising, e.g., analyzing Aβ by one or more techniques chosen from Western blot, immunoprecipitation, enzyme-linked immunosorbent assay (ELISA), radioimmunoassay (RIA), fluorescent activated cell sorting (FACS), two-dimensional gel electrophoresis, mass spectroscopy (MS), matrix-assisted laser desorption/ionization-time of flight-MS (MALDI-TOF), surface-enhanced laser desorption ionization-time of flight (SEMI-TOE), high performance liquid Chromatography (HPLC), fast protein liquid chromatography (FPLC), multidimensional liquid chromatography (LC) followed by tandem mass spectrometry (MS/MS), and laser densitometry. In vivo imaging of Aβ is particularly suited for evaluating amyloid plaque load. Non-limiting examples of in vivo imaging methods include positron emission tomography (PET), single photon emission tomography (SPECT), near infrared (NIR) optical imaging or magnetic resonance imaging (MRI). Suitable imaging agents are also known in the art (e.g. PIB, etc.).

In another embodiment, the disclosure provides a method for improving an Aβ plaque associated symptom and/or a CAA associated symptom in a subject. The method comprises administering a therapeutically effective amount of an anti-TREM-2 agonist antibody that specifically binds TREM-2 to a subject with at least one Aβ plaque associated symptom and/or at least one CAA associated symptom. Suitable anti-TREM-2 agonist antibodies include those disclosed herein. Non-limiting examples of improved Aβ plaque associated symptoms are identified above. In certain embodiments, improved Aβ plaque associated symptoms may include decreased inflammation, reduced neuronal degeneration, a delay in cognitive decline, improved cognitive function, improvement in an altered behavior, improved emotional dysregulation, and/or fewer seizures. In each of the above embodiments, the improvement (i.e. the change) in the symptom is at least statistically significant. In certain embodiments, the change may be at least 1, 2, 3, 4, 5, 6, 7, 8, 9, 10, 11, 12, 13, 14, 15, 16, 17, 18, 19, or 20% compared to untreated or negative control treated subjects. In some embodiments, the change may be at least 20, 25, 30, 35, 40, 45, 50, 55, 60, 65, 70, 75, 80, 85, 90, or 95% compared to untreated or negative control treated subjects. In other embodiments, the change may be at least 100, 125, 150, 200, 250, 300, 350, 400, or 450% compared to untreated or negative control treated subjects.

In another embodiment, the disclosure provides a method for increasing microglial survival and/or increasing Aβ plaque-associated microglia in a subject. The method comprises administering a therapeutically effective amount of an anti-TREM-2 agonist antibody that specifically binds TREM-2 to a subject with at least one Aβ plaque associated symptom and/or at least one CAA associated symptom. Suitable anti-TREM-2 agonist antibodies include those disclosed herein. Preferably the increase is statistically significant. In certain embodiments, the increase may be at least 1, 2, 3, 4, 5, 6, 7, 8, 9, 10, 11, 12, 13, 14, 15, 16, 17, 18, 19, or 20% compared to untreated or negative control treated subjects. In some embodiments, the increase may be at least 20, 25, 30, 35, 40, 45, 50, 55, 60, 65, 70, 75, 80, 85, 90, or 95% compared to untreated or negative control treated subjects. In other embodiments, the increase may be at least 100, 125, 150, 200, 250, 300, 350, 400, or 450% compared to untreated or negative control treated subjects.

For each of the above embodiments, suitable anti-TREM-2 agonist antibodies are described in Section II. In certain embodiments, an anti-TREM-2 agonist antibody is (a) an antibody selected from Table A, (b) an antibody selected from Table B, (c) an anti-TREM-2 agonist antibody that competitively inhibits HJ23.4, HJ23.7, HJ23.8, HJ23.9, HJ23.10 or HJ23.13 binding to human TREM-2, (d) HJ23.4, HJ23.7, HJ23.8, HJ23.9, HJ23.10 or HJ23.13, or (e) a humanized derivative of HJ23.4, HJ23.7. HJ23.8, HJ23.9, HJ23.10 or HJ23.13.

Anti-TREM-2 antibodies disclosed herein can also be conjugated to therapeutic agents, prodrugs, peptides, proteins, enzymes, viruses, biological response modifiers, pharmaceutical agents, or PEG. In certain embodiments, therapeutic agent may be a drug, a radioisotope, a lectin, or a toxin. Conjugates that are immunotoxins have been widely described in the art. The toxins can be coupled to the antibodies by conventional coupling techniques or immunotoxins containing protein toxin portions can be produced as fusion proteins. In using radioisotopically conjugated anti-TREM-2 antibodies for immunotherapy, certain isotopes can be chosen depending on such factors as leukocyte distribution as well as stability and emission. Depending on the autoimmune response, some emitters can be used. In general, a and B particle emitting radioisotopes are utilized in immunotherapy. In certain embodiments, short range, high energy a emitters such as 212Bi can be used. Examples of radioisotopes which can be bound to the anti-TREM-2 antibodies disclosed herein for therapeutic purposes include, but are not limited to $^{123}$I, $^{124}$I, $^{125}$I, $^{131}$I, $^{89}$Zr, $^{90}$Y, $^{67}$Cu, $^{64}$Cu, $^{111}$In, $^{212}$Bi, $^{212}$At, $^{211}$Pb, $^{47}$Sc, $^{109}$Pd, and $^{188}$Re. Other therapeutic agents which can be coupled to the anti-TREM-2 antibodies, as well as ex vivo and in vivo therapeutic protocols, are known, or can be easily ascertained, by those of ordinary skill in the art.

Administration of an anti-TREM-2 antibody, or a composition comprising an anti-TREM-2 antibody, is performed using standard effective techniques, include peripherally (i.e. not by administration into the central nervous system) or locally to the central nervous system. Peripheral administration includes but is not limited to intravenous, intraperitoneal, subcutaneous, pulmonary, transdermal, intramuscular, intranasal, buccal, sublingual, or suppository administration. Local administration, including directly into the central nervous system (CNS) includes but is not limited to via a lumbar, intraventricular or intraparenchymal catheter or using a surgically implanted controlled release formulation.

Pharmaceutical compositions for effective administration are deliberately designed to be appropriate for the selected mode of administration, and pharmaceutically acceptable excipients such as compatible dispersing agents, buffers, surfactants, preservatives, solubilizing agents, isotonicity agents, stabilizing agents and the like are used as appropriate. Remington's Pharmaceutical Sciences, Mack Publishing Co., Easton Pa., 16Ed ISBN: 0-912734-04-3, latest edition, incorporated herein by reference in its entirety, provides a compendium of formulation techniques as are generally known to practitioners. It may be particularly useful to alter the solubility characteristics of the antibodies useful in this discovery, making them more lipophilic, for example, by encapsulating them in liposomes or by blocking polar groups.

The concentration of antibody in formulations to be administered is an effective amount and ranges from as low as about 0.1% by weight to as much as about 15 or about 20% by weight and will be selected primarily based on fluid volumes, viscosities, and so forth, in accordance with the particular mode of administration selected if desired. A typical composition for injection to a living subject could be made up to contain 1 mL sterile buffered water of phosphate buffered saline and about 1-1000 mg of any one of or a combination of the antibodies disclosed herein. The formulation could be sterile filtered after making the formulation, or otherwise made microbiologically acceptable. A typical composition for intravenous infusion could have volumes between 1-250 ml of fluid, such as sterile Ringer's solution, and 1-100 mg per ml, or more in anti-TREM-2 antibody concentration. Anti-TREM-2 antibodies disclosed herein can be frozen or lyophilized for storage and reconstituted in a suitable sterile carrier prior to use. Lyophilization and reconstitution may lead to varying degrees of antibody activity loss (e.g. with conventional immune globulins, IgM antibodies tend to have greater activity loss than IgG antibodies). Dosages administered are effective dosages and may have to be adjusted to compensate. The pH of the formulations generally pharmaceutical grade quality, will be selected to balance antibody stability (chemical and physical) and comfort to the subject when administered. Generally, a pH between 4 and 8 is tolerated. Doses will vary from individual to individual based on size, weight, and other physiobiological characteristics of the individual receiving the successful administration.

As used herein, the term "therapeutically effective amount" means an amount of a substance (e.g. an anti-TREM-2 antibody) that leads to measurable and beneficial effects for the subject administered the substance, i.e., significant efficacy. The therapeutically effective amount or dose of compound administered according to this discovery will be determined using standard clinical techniques and may be by influenced by the circumstances surrounding the case, including the antibody administered, the route of administration, and the status of the symptoms being treated, among other considerations. A typical dose may contain from about 0.01 mg/kg to about 100 mg/kg of an anti-TREM-2 antibody described herein. Doses can range from about 0.05 mg/kg to about 50 mg/kg, more preferably from about 0.1 mg/kg to about 25 mg/kg. The frequency of dosing may be daily or once, twice, three times or more per week or per month, as needed as to effectively treat the symptoms.

The timing of administration of the treatment relative to the disease itself and duration of treatment will be determined by the circumstances surrounding the case. Duration of treatment could range from a single dose administered on a one-time basis to a life-long course of therapeutic treatments.

Although the foregoing methods appear the most convenient and most appropriate and effective for administration of proteins such as humanized antibodies, by suitable adaptation, other effective techniques for administration, such as intraventricular administration, transdermal administration and oral administration may be employed provided proper formulation is utilized herein. In addition, a person skilled in the art can use a polynucleotide of the invention encoding any one of the above-described antibodies instead of the proteinaceous material itself. For example, In addition, it may be desirable to employ controlled release formulations using biodegradable films and matrices, or osmotic mini-pumps, or delivery systems based on dextran beads, alginate, or collagen.

IV. Diagnosing or Tracking Methods

The present disclosure also provides anti-TREM-2 antibodies conjugated to a detectable signal (i.e. a measurable substance, or a substance that generates a measurable signal). Non-limiting examples include various enzymes, prosthetic groups, fluorescent materials, luminescent materials, bioluminescent materials, radioactive materials, positron emitting metals using various positron emission tomographies, and nonradioactive paramagnetic metal ions. See, e.g., U.S. Pat. No. 4,741,900 for metal ions which can be conjugated to antibodies for use as diagnostics according to the disclosure. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}$I, $^{131}$I, $^{111}$In or $^{99}$Tc. The signal generated by the agent can be measured, for example, by single-photon emission computed tomography (SPECT) or positron emission tomography (PET).

Anti-TREM-2 antibodies conjugated to a detectable signal may be used diagnostically to, for example, monitor the development or progression of a neurodegenerative disease as part of a clinical testing procedure to, e.g., determine the efficacy of a given treatment and/or prevention regimen. The patient's treatment can be adjusted based on the level of neurodegenerative disease progression.

In some embodiments, a method of assessing disease progression in a subject being treated for a neurodegenerative disease characterized by brain amyloid plaques or a neurodegenerative disease characterized by vascular amyloid plaques in the brain is provided, the method comprising: (a) administering an anti-TREM-2 antibody disclosed herein that is labeled with an agent that generates a measurable signal as described herein (i.e. "labeled ant-TREM-2 antibody"), wherein the signal is measured in the patient following the administration; (b) administering the labeled anti-TREM-2 or antigen-binding fragment thereof at one or more time intervals following the administration of (a), wherein the signal is measured in the patient following the administration; and (c) assessing disease progression in the patient based on a change in the signal measured in the patient at the one or more time intervals following administration of (a); wherein an increase in the signal indicates progression of the neurodegenerative disease in the patient. In certain embodiments, the subject is being treated with the same anti-TREM-2 antibody, but in an unlabeled form. In certain embodiments, the subject is being treated with an anti-TREM-2 antibody that competitively inhibits the labeled ant-TREM-2 antibody binding to human TREM-2. In certain embodiments, the subject is being treated with an anti-TREM-2 antibody that does not competitively inhibit the labeled anti-TREM-2 antibody binding to human TREM-2. In certain embodiments, the subject is being treated with other drugs known in the art.

In other embodiments, a method of assessing disease progression in a subject being treated for a neurodegenerative disease characterized by brain amyloid plaques or a neurodegenerative disease characterized by vascular amyloid plaques in the brain is provided, the method comprising: (a) administering an anti-TREM-2 antibody disclosed herein that is labeled with an agent that generates a measurable signal as described herein (i.e. "labeled anti-TREM-2 antibody"), wherein the signal is measured in the patient following the administration; (b) assessing the disease state in the subject upon review of a comparison of the signal measured in the subject to the signal measured following administration of the labeled antibody or antigen-binding fragment thereof to one or more control subjects; wherein an increase in the signal generated in the patient relative to the control subject correlates with an increase in brain amyloid plaques; and (c) treating the patient with a therapy appropriate for the patient's disease state. A "control subject(s)," refers to any normal healthy subject (or a pool of subjects), a subject or subjects with different degrees of disease, or even the actual test subject at an earlier stage of disease. In certain embodiments, the therapy is the same anti-TREM-2 antibody, but in an unlabeled form. In certain embodiments, the therapy is an anti-TREM-2 antibody that competitively inhibits the labeled anti-TREM-2 antibody binding to human TREM-2. In certain embodiments, the therapy is an anti-TREM-2 antibody that does not competitively inhibit the labeled anti-TREM-2 antibody binding to human TREM-2. In certain embodiments, the therapy is with an anti-Aβ antibody, an anti-tau antibody, a gamma-secretase inhibitor, a beta-secretase inhibitor, a cholinesterase inhibitor, an NMDA receptor antagonist, or other drugs known in the art.

The present disclosure also provides the use of the anti-TREM-2 antibodies disclosed herein for measuring the amount of brain amyloid plaques in a test subject, assessing disease progression in a patient being treated for a neurodegenerative disease or treating a neurodegenerative disease characterized by brain amyloid plaques in a patient in need of treatment.

V. Pharmaceutical Compositions

The present disclosure encompasses pharmaceutical compositions comprising an anti-TREM-2 antibody disclosed in Section II, so as to facilitate administration and promote stability of the active agent. For example, an anti-TREM-2 antibody of this disclosure may be admixed with at least one pharmaceutically acceptable carrier or excipient resulting in a pharmaceutical composition which is capably and effectively administered (given) to a living subject, such as to a suitable subject (i.e. "a subject in need of treatment" or "a subject in need thereof"). Methods of preparing and administering anti-TREM-2 antibodies disclosed herein to a subject in need thereof are well known to or are readily determined by those skilled in the art. The route of administration of an anti-TREM-2 antibody can be, for example, peripheral, oral, parenteral, by inhalation or topical.

Pharmaceutical compositions for effective administration are deliberately designed to be appropriate for the selected mode of administration, and pharmaceutically acceptable excipients such as compatible carriers, dispersing agents, buffers, surfactants, preservatives, solubilizing agents, isotonicity agents, stabilizing agents and the like are used as appropriate.

Non-limiting examples of pharmaceutically acceptable carriers, include physiological saline, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol, wool fat or a combination thereof.

Prevention of the action of microorganisms can be achieved by various antibacterial and antifungal agents, for example, parabens, chlorobutanol, phenol, ascorbic acid, thimerosal and the like. In many cases, isotonic agents can be included, for example, sugars, polyalcohols, such as mannitol, sorbitol, or sodium chloride in the composition.

Prolonged absorption of the injectable compositions can be brought about by including in the composition an agent which delays absorption, for example, aluminum monostearate and gelatin.

Compositions disclosed herein can be frozen or lyophilized for storage and reconstituted in a suitable sterile carrier prior to use.

In some embodiments, anti-TREM-2 antibodies may be formulated for parenteral administration. Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives can also be present such as, for example, antimicrobials, anti-oxidants, chelating agents, and inert gases and the like. Parenteral formulations can be a single bolus dose, an infusion or a loading bolus dose followed with a maintenance dose. These compositions can be administered at specific fixed or variable intervals, e.g., once a day, or on an "as needed" basis.

Certain pharmaceutical compositions, as disclosed herein, can be orally administered in an acceptable dosage form including, e.g., capsules, tablets, aqueous suspensions or solutions. Certain pharmaceutical compositions also can be administered by nasal aerosol or inhalation. Such compositions can be prepared as solutions in saline, employing benzyl alcohol or other suitable preservatives, absorption promoters to enhance bioavailability, and/or other conventional solubilizing or dispersing agents.

The amount of an anti-TREM-2 antibody to be combined with the carrier materials to produce a single dosage form will vary depending upon the host treated and the particular mode of administration. The composition can be administered as a single dose, multiple doses or over an established period of time in an infusion. Dosage regimens also can be adjusted to provide the optimum desired response (e.g., a therapeutic or prophylactic response).

EXAMPLES

The following examples are included to demonstrate preferred embodiments of the invention. It should be appreciated by those of skill in the art that the techniques disclosed in the examples that follow represent techniques discovered by the inventors to function well in the practice of the invention. Those of skill in the art should, however, in light of the present disclosure, appreciate that many changes can be made in the specific embodiments that are disclosed and still obtain a like or similar result without departing from the spirit and scope of the invention, therefore all matter set forth or shown in the accompanying examples and drawings is to be interpreted as illustrative and not in a limiting sense.

Example 1

Murine monoclonal antibodies to TREM-2 were generated and sequenced. Briefly, to generate the antibodies, a human TREM-2 fragment (SEQ ID NO: 43) fused to Keyhole Limpet hemocyanin (KLH) was injected intraperitoneally (IP) into a wildtype mouse on a B6C3 background. 100 µg of antigen (in 200 µl PBS+200 µl complete Freund's adjuvant) was injected on day 0, day 14 and day 28. A last boost of 50 µg of antigen in PBS was injected IP 3 days before fusion of myeloma cells with spleen cells of the mice. Serum was tested by direct ELISA to TREM-2 on day 21 and day 35. If titer was over 1:10,000, myeloma cells were then fused with mouse spleen cells per standard protocol, followed by isolation of hybridoma clones.

TABLE 1

| Antibody (ATCC # of the hybridoma) | Light chain variable region | Heavy chain variable region |
|---|---|---|
| HJ23.4 (PTA-125168) | SEQ ID NO: 1 | SEQ ID NO: 2 |
| HJ23.7 (PTA-125169) | SEQ ID NO: 8 | SEQ ID NO: 9 |
| HJ23.8 (PTA-125170) | SEQ ID NO: 15 | SEQ ID NO: 16 |
| HJ23.9 (PTA-125171) | SEQ ID NO: 23 | SEQ ID NO: 23 |
| HJ23.10 (PTA-125172) | SEQ ID NO: 29 | SEQ ID NO: 30 |
| HJ23.13 (PTA-125173) | SEQ ID NO: 36 | SEQ ID NO: 37 |

Example 2

To assess TREM-2 binding, antibodies were screened by ELISA using bacterial-produced or mammalian-produced TREM-2. To assess activity, a dose-response curve was generated using 2B4 cells that exogenously express human TREM2 and an NFAT-GFP reporter. In this cell line, TREM2 activation leads to elevation of intracellular calcium, which results in NFAT-dependent GFP expression.

Briefly, a 96-well thin clear bottom plate was coated overnight at 4° C. with 100 µL of antibody in carbonate buffer (pH 9.6) at concentrations ranging from 1 nM to 1000 nM. Plates were rinsed with PBS and 2B4 cells stably co-expressing human TREM2 and a GFP reporter gene driven by an NFAT-responsive promoter were seeded at 50,000 cells per well. 24 hours later the cells were imaged on a BioTek Cytation 5 instrument and the percentage of GFP-expressing cells was calculated. Cells that expressed the GFP reporter gene, but not TREM2, were used as a negative control and did not exhibit any response to antibodies (FIG. 1).

| SEQ ID NO | Comments | Sequence |
|---|---|---|
| 1 | HJ23.4 light chain variable region | DVVMTQTPLSLPVSLGDQAFISCRSSQNLVHSNGNTYLHWYLQ KPGQSPKLLIYIVSNRFSGVPDRFSGSGSGTDFTLEISRVEAEDL GVYFCSQSTHVPLTFGAGTKLELK |
| 2 | HJ23.4 heavy chain variable region | EVQLQQSGPDLVKPGASVKMSCKASGYTFTDYNIHWVKQSHG KTLEWIGYINPNTGGTYYNQKFKGKATMTVNKSSSTAYMELRSL TSEDSAVYYCVATRWDGVNWAQGTLVTVSA |
| 3 | HJ23.4 L1 | QNLVHSNGNTY |
|  | HJ23.4 L2 | IVS |
| 4 | HJ23.4 L3 | SQSTHVPLT |
| 5 | HJ23.4 H1 | GYTFTDYN |
| 6 | HJ23.4 H2 | INPNTGGT |
| 7 | HJ23.4 H3 | VATRWDGVN |
| 8 | HJ23.7 light chain variable region | DVVMTQTPLSLPVSLGDQASISCRSSQSLVHSNGNTYLHWYLQ KPGQSPKLLIYKVSNRFSGVPDRFSGSGSGTDFTLKISRVEAED LGVYFCSQSTHVPLTFGAGTKLELK |
| 9 | HJ23.7 heavy chain variable region | EVQLQQSGAELVKPGASVKLSCTSSGFNIKGYYIHWVKQRTEQ GLEWIGRIDPEDGETKNAPKFQGKATFGTDTFSNTAYLRLSSLT SEDTGVYYCVRTETRGAYWGPGTLVTVSA |
| 10 | HJ23.7 L1 | QSLVHSNGNTY |
|  | HJ23.7 L2 | KVS |
| 11 | HJ23.7 L3 | SQSTHVPLT |
| 12 | HJ23.7 H1 | GFNIKGYY |
| 13 | HJ23.7 H2 | IDPEDGET |

-continued

| SEQ ID NO | Comments | Sequence |
|---|---|---|
| 14 | HJ23.7 H3 | VRTETRGAY |
| 15 | HJ23.8 light chain variable region | DVVMTQTPLSLPVSLGDQASISCRSSQSLVHSNGDTYLHWYLQ KRGQSPKLLIYKVSNRFSGVPDRFSGSGSGTDFTLKISRVEAED LGVYFCSQTTHVPLTFGAGTKLELK |
| 16 | HJ23.8 heavy chain variable region | QVPLQQPGAEFVKPGASVKLSCKASAYTFTRYWMHWVKQRPG RGLEWIGRIDPNSGGTNYNEKFKSKATFTVDKPSSTSYMQLSSL TSEDSAVYFCVFTGTLFDYWGQGTTLTVSS |
| 17 | HJ23.8 L1 | QSLVHSNGDTY |
|  | HJ23.8 L2 | KVS |
| 18 | HJ23.8 L3 | SQTTHVPLT |
| 19 | HJ23.8 H1 | AYTFTRYW |
| 20 | HJ23.8 H2 | IDPNSGGT |
| 21 | HJ23.8 H3 | VFTGTLFDY |
| 22 | HJ23.9 light chain variable region | DVVMTQTPLSLPVSLGDQASISCKSSQSLVHSNGNTYLHWYLQ KPGQSPKLLIYKVSNRFSGVPDRFSGSGSGTDFTLKISRVEAED LGVYFCSQSTHVPPTFGGGTKLEIK |
| 23 | HJ23.9 heavy chain variable region | EVQLQHSGPVLVKPGASVKMSCKSSGYTFTDYYLNWVKQSHG KSPEWIGVINPNTGSTSYNQKFKGKATLTVDKSSSTAYMDLNSL TSEDSAVYYCATHYYGSIYKQAWFAYWGQGTLVT |
| 24 | HJ23.9 L1 | QSLVHSNGNTY |
|  | HJ23.9 L2 | KVS |
| 25 | HJ23.9 L3 | SQSTHVPPT |
| 26 | HJ23.9 H1 | GYTFTDYY |
| 27 | HJ23.9 H2 | INPNTGST |
| 28 | HJ23.9 H3 | ATHYYGSIYKQAWFAY |
| 29 | HJ23.10 light chain variable region | DVVMTQTPLSLPVSLGDQASISCKSSQSLVHSNGNTYLHWYLQ KPGQSPKLLIYKVSNRFSGVPDRFSGSGSGTDFTLKISRVEAED LGIYFCSQSTHVPPTFGGGTKLEIK |
| 30 | HJ23.10 heavy chain variable region | EVQLQHSGPVLVKPGASVKMSCKASGYTFTDYYMNWVKQSHG KSPEWIGVINPNTGSTSYNQKFKGKATLTVDKSSSTAYMDLNSL TSEDSAVYYCATHYYGSIYKQAWFAYWGQGTLVTV |
| 31 | HJ23.10 L1 | QSLVHSNGNTY |
|  | HJ23.10 L2 | KVS |
| 32 | HJ23.10 L3 | SQSTHVPPT |
| 33 | HJ23.10 H1 | GYTFTDYY |
| 34 | HJ23.10 H2 | INPNTGST |
| 35 | HJ23.10 H3 | ATHYYGSIYKQAWFAY |
| 36 | HJ23.13 light chain variable region | DIVMSQSPSSLAVSVGEKVTMSCKSSQSLLYSSNLKNYLAWFQ QKPGQSPKLLIYWASIRESGVPDRFTGSGSGTDFTLTINSVKAE DLAVYYCQQYYTFPLTFGAGTKLELK |
| 37 | HJ23.13 heavy chain variable region | EVQLVETGGGLVQPKGSLKLSCAASGFSFNINAMHWVRQAPGT GLKWVARIRSGSNDFATYYADSVKDRFTISRDDSHSMLYLQMN NLKTEDTAIYFCVREYVNYFVHWGQGTLVTVSA |
| 38 | HJ23.13 L1 | QSLLYSSNLKNY |
|  | HJ23.13 L2 | WAS |
| 39 | HJ23.13 L3 | QQYYTFPLT |

| SEQ ID NO | Comments | Sequence |
|---|---|---|
| 40 | HJ23.13 H1 | GFSFNINA |
| 41 | HJ23.13 H2 | IRSGSNDFAT |
| 42 | HJ23.13 H3 | VREYVNYFVH |
| 43 | | DHRDAGDLWFPGES |
| 44 | Consensus L1 | QX$^1$LVHSNGX$^2$TY, where X$^1$ is S, T, N, or Q and X$^2$ is D or N |
| | Consensus L2 | X$^1$VS, where X$^1$ is I or K |
| 45 | Consensus L3 | SQX$^1$THVPX$^2$T, where X$^1$ is S, T, N, or Q and X$^2$ is P or L |

What is claimed is:

1. An isolated anti-TREM-2 antibody comprising (a) a light chain variable region comprising an L1 of SEQ ID NO: 17, an L2 comprising the amino acid sequence KVS, and an L3 of SEQ ID NO: 18; and (b) a heavy chain variable region comprising an H1 of SEQ ID NO: 19, an H2 of SEQ ID NO: 20, and an H3 of SEQ ID NO: 21.

2. The isolated antibody of claim 1, wherein the amino acid sequence of the light chain variable region is SEQ ID NO: 15.

3. The isolated antibody of claim 1, wherein the amino acid sequence of the heavy chain variable region is SEQ ID NO: 16.

4. The isolated antibody of claim 1, wherein the amino acid sequence of the light chain variable region is SEQ ID NO: 15 and the amino acid sequence of the heavy chain variable region is SEQ ID NO: 16.

5. The isolated antibody of claim 1, wherein the framework region of each variable region comprises a human framework region sequence.

6. The isolated antibody of claim 1, wherein the antibody is a monoclonal antibody or an antibody fragment.

7. A pharmaceutical composition comprising the isolated antibody of claim 1 and a pharmaceutically acceptable carrier or excipient.

8. The pharmaceutical composition of claim 7, further comprising a dispersing agent, buffer, surfactant, preservative, solubilizing agent, isotonicity agent, or stabilizing agent.

9. The pharmaceutical composition of claim 7, wherein said carrier comprises physiological saline, ion exchanger, alumina, aluminum stearate, lecithin, serum protein, human serum albumin, buffer, phosphate, glycine, sorbic acid, potassium sorbate, partial glyceride mixture of saturated vegetable fatty acids, water, salts or electrolytes, protamine sulfate, disodium hydrogen phosphate, potassium hydrogen phosphate, sodium chloride, zinc salt, colloidal silica, magnesium trisilicate, polyvinyl pyrrolidone, cellulose, polyethylene glycol, sodium carboxymethylcellulose, polyacrylates, wax, polyethylene-polyoxypropylene-block polymer, polyethylene glycol, wool fat, or a combination thereof.

\* \* \* \* \*

SEQUENCE LISTING

<160> NUMBER OF SEQ ID NOS: 45

<210> SEQ ID NO 1
<211> LENGTH: 112
<212> TYPE: PRT
<213> ORGANISM: Artificial Sequence
<220> FEATURE:
<223> OTHER INFORMATION: SYNTHESIZED

<400> SEQUENCE: 1

```
Asp Val Val Met Thr Gln Thr Pro Leu Ser Leu Pro Val Ser Leu Gly
1               5                   10                  15
Asp Gln Ala Phe Ile Ser Cys Arg Ser Ser Gln Asn Leu Val His Ser
            20                  25                  30
Asn Gly Asn Thr Tyr Leu His Trp Tyr Leu Gln Lys Pro Gly Gln Ser
        35                  40                  45
Pro Lys Leu Leu Ile Tyr Ile Val Ser Asn Arg Phe Ser Gly Val Pro
    50                  55                  60
Asp Arg Phe Ser Gly Ser Gly Ser Gly Thr Asp Phe Thr Leu Glu Ile
65                  70                  75                  80
Ser Arg Val Glu Ala Glu Asp Leu Gly Val Tyr Phe Cys Ser Gln Ser
                85                  90                  95
Thr His Val Pro Leu Thr Phe Gly Ala Gly Thr Lys Leu Glu Leu Lys
                100                 105                 110
```

<210> SEQ ID NO 2
<211> LENGTH: 116
<212> TYPE: PRT
<213> ORGANISM: Artificial Sequence
<220> FEATURE:
<223> OTHER INFORMATION: SYNTHESIZED

<400> SEQUENCE: 2

```
Glu Val Gln Leu Gln Gln Ser Gly Pro Asp Leu Val Lys Pro Gly Ala
1               5                   10                  15
Ser Val Lys Met Ser Cys Lys Ala Ser Gly Tyr Thr Phe Thr Asp Tyr
            20                  25                  30
Asn Ile His Trp Val Lys Gln Ser His Gly Lys Thr Leu Glu Trp Ile
        35                  40                  45
Gly Tyr Ile Asn Pro Asn Thr Gly Gly Thr Tyr Asn Gln Lys Phe
    50                  55                  60
Lys Gly Lys Ala Thr Met Thr Val Asn Lys Ser Ser Ser Thr Ala Tyr
```

```
                65                  70                  75                  80
Met Glu Leu Arg Ser Leu Thr Ser Glu Asp Ser Ala Val Tyr Tyr Cys
                    85                  90                  95
Val Ala Thr Arg Trp Asp Gly Val Asn Trp Ala Gln Gly Thr Leu Val
                100                 105                 110

Thr Val Ser Ala
        115

<210> SEQ ID NO 3
<211> LENGTH: 11
<212> TYPE: PRT
<213> ORGANISM: Artificial Sequence
<220> FEATURE:
<223> OTHER INFORMATION: SYNTHESIZED

<400> SEQUENCE: 3

Gln Asn Leu Val His Ser Asn Gly Asn Thr Tyr
1               5                   10

<210> SEQ ID NO 4
<211> LENGTH: 9
<212> TYPE: PRT
<213> ORGANISM: Artificial Sequence
<220> FEATURE:
<223> OTHER INFORMATION: SYNTHESIZED

<400> SEQUENCE: 4

Ser Gln Ser Thr His Val Pro Leu Thr
1               5

<210> SEQ ID NO 5
<211> LENGTH: 8
<212> TYPE: PRT
<213> ORGANISM: Artificial Sequence
<220> FEATURE:
<223> OTHER INFORMATION: SYNTHESIZED

<400> SEQUENCE: 5

Gly Tyr Thr Phe Thr Asp Tyr Asn
1               5

<210> SEQ ID NO 6
<211> LENGTH: 8
<212> TYPE: PRT
<213> ORGANISM: Artificial Sequence
<220> FEATURE:
<223> OTHER INFORMATION: SYNTHESIZED

<400> SEQUENCE: 6

Ile Asn Pro Asn Thr Gly Gly Thr
1               5

<210> SEQ ID NO 7
<211> LENGTH: 9
<212> TYPE: PRT
<213> ORGANISM: Artificial Sequence
<220> FEATURE:
<223> OTHER INFORMATION: SYNTHESIZED

<400> SEQUENCE: 7

Val Ala Thr Arg Trp Asp Gly Val Asn
1               5

<210> SEQ ID NO 8
<211> LENGTH: 112
```

```
<212> TYPE: PRT
<213> ORGANISM: Artificial Sequence
<220> FEATURE:
<223> OTHER INFORMATION: SYNTHESIZED

<400> SEQUENCE: 8

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Leu Thr Phe Gly Ala Gly Thr Lys Leu Glu Leu Lys
            100                 105                 110

<210> SEQ ID NO 9
<211> LENGTH: 116
<212> TYPE: PRT
<213> ORGANISM: Artificial Sequence
<220> FEATURE:
<223> OTHER INFORMATION: SYNTHESIZED

<400> SEQUENCE: 9

Glu Val Gln Leu Gln Gln Ser Gly Ala Glu Leu Val Lys Pro Gly Ala
1               5                   10                  15

Ser Val Lys Leu Ser Cys Thr Ser Ser Gly Phe Asn Ile Lys Gly Tyr
            20                  25                  30

Tyr Ile His Trp Val Lys Gln Arg Thr Glu Gln Gly Leu Glu Trp Ile
        35                  40                  45

Gly Arg Ile Asp Pro Glu Asp Gly Glu Thr Lys Asn Ala Pro Lys Phe
    50                  55                  60

Gln Gly Lys Ala Thr Phe Gly Thr Asp Thr Phe Ser Asn Thr Ala Tyr
65                  70                  75                  80

Leu Arg Leu Ser Ser Leu Thr Ser Glu Asp Thr Gly Val Tyr Tyr Cys
                85                  90                  95

Val Arg Thr Glu Thr Arg Gly Ala Tyr Trp Gly Pro Gly Thr Leu Val
            100                 105                 110

Thr Val Ser Ala
        115

<210> SEQ ID NO 10
<211> LENGTH: 11
<212> TYPE: PRT
<213> ORGANISM: Artificial Sequence
<220> FEATURE:
<223> OTHER INFORMATION: SYNTHESIZED

<400> SEQUENCE: 10

Gln Ser Leu Val His Ser Asn Gly Asn Thr Tyr
1               5                   10

<210> SEQ ID NO 11
<211> LENGTH: 9
<212> TYPE: PRT
```

```
<213> ORGANISM: Artificial Sequence
<220> FEATURE:
<223> OTHER INFORMATION: SYNTHESIZED

<400> SEQUENCE: 11

Ser Gln Ser Thr His Val Pro Leu Thr
1               5

<210> SEQ ID NO 12
<211> LENGTH: 8
<212> TYPE: PRT
<213> ORGANISM: Artificial Sequence
<220> FEATURE:
<223> OTHER INFORMATION: SYNTHESIZED

<400> SEQUENCE: 12

Gly Phe Asn Ile Lys Gly Tyr Tyr
1               5

<210> SEQ ID NO 13
<211> LENGTH: 8
<212> TYPE: PRT
<213> ORGANISM: Artificial Sequence
<220> FEATURE:
<223> OTHER INFORMATION: SYNTHESIZED

<400> SEQUENCE: 13

Ile Asp Pro Glu Asp Gly Glu Thr
1               5

<210> SEQ ID NO 14
<211> LENGTH: 9
<212> TYPE: PRT
<213> ORGANISM: Artificial Sequence
<220> FEATURE:
<223> OTHER INFORMATION: SYNTHESIZED

<400> SEQUENCE: 14

Val Arg Thr Glu Thr Arg Gly Ala Tyr
1               5

<210> SEQ ID NO 15
<211> LENGTH: 112
<212> TYPE: PRT
<213> ORGANISM: Artificial Sequence
<220> FEATURE:
<223> OTHER INFORMATION: SYNTHESIZED

<400> SEQUENCE: 15

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asp Thr Tyr Leu His Trp Tyr Leu Gln Lys Arg Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Thr
                85                  90                  95

Thr His Val Pro Leu Thr Phe Gly Ala Gly Thr Lys Leu Glu Leu Lys
            100                 105                 110
```

```
<210> SEQ ID NO 16
<211> LENGTH: 116
<212> TYPE: PRT
<213> ORGANISM: Artificial Sequence
<220> FEATURE:
<223> OTHER INFORMATION: SYNTHESIZED

<400> SEQUENCE: 16

Gln Val Pro Leu Gln Gln Pro Gly Ala Glu Phe Val Lys Pro Gly Ala
1               5                   10                  15

Ser Val Lys Leu Ser Cys Lys Ala Ser Ala Tyr Thr Phe Thr Arg Tyr
            20                  25                  30

Trp Met His Trp Val Lys Gln Arg Pro Gly Arg Gly Leu Glu Trp Ile
        35                  40                  45

Gly Arg Ile Asp Pro Asn Ser Gly Gly Thr Asn Tyr Asn Glu Lys Phe
    50                  55                  60

Lys Ser Lys Ala Thr Phe Thr Val Asp Lys Pro Ser Ser Thr Ser Tyr
65                  70                  75                  80

Met Gln Leu Ser Ser Leu Thr Ser Glu Asp Ser Ala Val Tyr Phe Cys
                85                  90                  95

Val Phe Thr Gly Thr Leu Phe Asp Tyr Trp Gly Gln Gly Thr Thr Leu
            100                 105                 110

Thr Val Ser Ser
        115

<210> SEQ ID NO 17
<211> LENGTH: 11
<212> TYPE: PRT
<213> ORGANISM: Artificial Sequence
<220> FEATURE:
<223> OTHER INFORMATION: SYNTHESIZED

<400> SEQUENCE: 17

Gln Ser Leu Val His Ser Asn Gly Asp Thr Tyr
1               5                   10

<210> SEQ ID NO 18
<211> LENGTH: 9
<212> TYPE: PRT
<213> ORGANISM: Artificial Sequence
<220> FEATURE:
<223> OTHER INFORMATION: SYNTHESIZED

<400> SEQUENCE: 18

Ser Gln Thr Thr His Val Pro Leu Thr
1               5

<210> SEQ ID NO 19
<211> LENGTH: 8
<212> TYPE: PRT
<213> ORGANISM: Artificial Sequence
<220> FEATURE:
<223> OTHER INFORMATION: SYNTHESIZED

<400> SEQUENCE: 19

Ala Tyr Thr Phe Thr Arg Tyr Trp
1               5

<210> SEQ ID NO 20
<211> LENGTH: 8
<212> TYPE: PRT
<213> ORGANISM: Artificial Sequence
<220> FEATURE:
```

-continued

<223> OTHER INFORMATION: SYNTHESIZED

<400> SEQUENCE: 20

Ile Asp Pro Asn Ser Gly Gly Thr
1               5

<210> SEQ ID NO 21
<211> LENGTH: 9
<212> TYPE: PRT
<213> ORGANISM: Artificial Sequence
<220> FEATURE:
<223> OTHER INFORMATION: VFTGTLFDY

<400> SEQUENCE: 21

Val Phe Thr Gly Thr Leu Phe Asp Tyr
1               5

<210> SEQ ID NO 22
<211> LENGTH: 112
<212> TYPE: PRT
<213> ORGANISM: Artificial Sequence
<220> FEATURE:
<223> OTHER INFORMATION: SYNTHESIZED

<400> SEQUENCE: 22

Asp Val Val Met Thr Gln Thr Pro Leu Ser Leu Pro Val Ser Leu Gly
1               5                   10                  15

Asp Gln Ala Ser Ile Ser Cys Lys Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Pro Thr Phe Gly Gly Gly Thr Lys Leu Glu Ile Lys
            100                 105                 110

<210> SEQ ID NO 23
<211> LENGTH: 120
<212> TYPE: PRT
<213> ORGANISM: Artificial Sequence
<220> FEATURE:
<223> OTHER INFORMATION: SYNTHESIZED

<400> SEQUENCE: 23

Glu Val Gln Leu Gln His Ser Gly Pro Val Leu Val Lys Pro Gly Ala
1               5                   10                  15

Ser Val Lys Met Ser Cys Lys Ser Ser Gly Tyr Thr Phe Thr Asp Tyr
            20                  25                  30

Tyr Leu Asn Trp Val Lys Gln Ser His Gly Lys Ser Pro Glu Trp Ile
        35                  40                  45

Gly Val Ile Asn Pro Asn Thr Gly Ser Thr Ser Tyr Asn Gln Lys Phe
    50                  55                  60

Lys Gly Lys Ala Thr Leu Thr Val Asp Lys Ser Ser Ser Thr Ala Tyr
65                  70                  75                  80

Met Asp Leu Asn Ser Leu Thr Ser Glu Asp Ser Ala Val Tyr Tyr Cys
                85                  90                  95

```
Ala Thr His Tyr Tyr Gly Ser Ile Tyr Lys Gln Ala Trp Phe Ala Tyr
            100                 105                 110
Trp Gly Gln Gly Thr Leu Val Thr
        115                 120

<210> SEQ ID NO 24
<211> LENGTH: 11
<212> TYPE: PRT
<213> ORGANISM: Artificial Sequence
<220> FEATURE:
<223> OTHER INFORMATION: SYNTHESIZED

<400> SEQUENCE: 24

Gln Ser Leu Val His Ser Asn Gly Asn Thr Tyr
1               5                   10

<210> SEQ ID NO 25
<211> LENGTH: 9
<212> TYPE: PRT
<213> ORGANISM: Artificial Sequence
<220> FEATURE:
<223> OTHER INFORMATION: SYNTHESIZED

<400> SEQUENCE: 25

Ser Gln Ser Thr His Val Pro Pro Thr
1               5

<210> SEQ ID NO 26
<211> LENGTH: 8
<212> TYPE: PRT
<213> ORGANISM: Artificial Sequence
<220> FEATURE:
<223> OTHER INFORMATION: SYNTHESIZED

<400> SEQUENCE: 26

Gly Tyr Thr Phe Thr Asp Tyr Tyr
1               5

<210> SEQ ID NO 27
<211> LENGTH: 8
<212> TYPE: PRT
<213> ORGANISM: Artificial Sequence
<220> FEATURE:
<223> OTHER INFORMATION: SYNTHESIZED

<400> SEQUENCE: 27

Ile Asn Pro Asn Thr Gly Ser Thr
1               5

<210> SEQ ID NO 28
<211> LENGTH: 16
<212> TYPE: PRT
<213> ORGANISM: Artificial Sequence
<220> FEATURE:
<223> OTHER INFORMATION: SYNTHESIZED

<400> SEQUENCE: 28

Ala Thr His Tyr Tyr Gly Ser Ile Tyr Lys Gln Ala Trp Phe Ala Tyr
1               5                   10                  15

<210> SEQ ID NO 29
<211> LENGTH: 112
<212> TYPE: PRT
<213> ORGANISM: Artificial Sequence
<220> FEATURE:
<223> OTHER INFORMATION: SYNTHESIZED
```

```
<400> SEQUENCE: 29

Asp Val Val Met Thr Gln Thr Pro Leu Ser Leu Pro Val Ser Leu Gly
1               5                   10                  15

Asp Gln Ala Ser Ile Ser Cys Lys Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Ile Tyr Phe Cys Ser Gln Ser
                85                  90                  95

Thr His Val Pro Pro Thr Phe Gly Gly Gly Thr Lys Leu Glu Ile Lys
            100                 105                 110

<210> SEQ ID NO 30
<211> LENGTH: 121
<212> TYPE: PRT
<213> ORGANISM: Artificial Sequence
<220> FEATURE:
<223> OTHER INFORMATION: SYNTHESIZED

<400> SEQUENCE: 30

Glu Val Gln Leu Gln His Ser Gly Pro Val Leu Val Lys Pro Gly Ala
1               5                   10                  15

Ser Val Lys Met Ser Cys Lys Ala Ser Gly Tyr Thr Phe Thr Asp Tyr
            20                  25                  30

Tyr Met Asn Trp Val Lys Gln Ser His Gly Lys Ser Pro Glu Trp Ile
        35                  40                  45

Gly Val Ile Asn Pro Asn Thr Gly Ser Thr Ser Tyr Asn Gln Lys Phe
    50                  55                  60

Lys Gly Lys Ala Thr Leu Thr Val Asp Lys Ser Ser Thr Ala Tyr
65                  70                  75                  80

Met Asp Leu Asn Ser Leu Thr Ser Glu Asp Ser Ala Val Tyr Tyr Cys
                85                  90                  95

Ala Thr His Tyr Tyr Gly Ser Ile Tyr Lys Gln Ala Trp Phe Ala Tyr
            100                 105                 110

Trp Gly Gln Gly Thr Leu Val Thr Val
            115                 120

<210> SEQ ID NO 31
<211> LENGTH: 11
<212> TYPE: PRT
<213> ORGANISM: Artificial Sequence
<220> FEATURE:
<223> OTHER INFORMATION: SYNTHESIZED

<400> SEQUENCE: 31

Gln Ser Leu Val His Ser Asn Gly Asn Thr Tyr
1               5                   10

<210> SEQ ID NO 32
<211> LENGTH: 9
<212> TYPE: PRT
<213> ORGANISM: Artificial Sequence
<220> FEATURE:
<223> OTHER INFORMATION: SYNTHESIZED

<400> SEQUENCE: 32
```

Ser Gln Ser Thr His Val Pro Pro Thr
1               5

<210> SEQ ID NO 33
<211> LENGTH: 8
<212> TYPE: PRT
<213> ORGANISM: Artificial Sequence
<220> FEATURE:
<223> OTHER INFORMATION: SYNTHESIZED

<400> SEQUENCE: 33

Gly Tyr Thr Phe Thr Asp Tyr Tyr
1               5

<210> SEQ ID NO 34
<211> LENGTH: 8
<212> TYPE: PRT
<213> ORGANISM: Artificial Sequence
<220> FEATURE:
<223> OTHER INFORMATION: SYNTHESIZED

<400> SEQUENCE: 34

Ile Asn Pro Asn Thr Gly Ser Thr
1               5

<210> SEQ ID NO 35
<211> LENGTH: 16
<212> TYPE: PRT
<213> ORGANISM: Artificial Sequence
<220> FEATURE:
<223> OTHER INFORMATION: SYNTHESIZED

<400> SEQUENCE: 35

Ala Thr His Tyr Tyr Gly Ser Ile Tyr Lys Gln Ala Trp Phe Ala Tyr
1               5                   10                  15

<210> SEQ ID NO 36
<211> LENGTH: 113
<212> TYPE: PRT
<213> ORGANISM: Artificial Sequence
<220> FEATURE:
<223> OTHER INFORMATION: SYNTHESIZED

<400> SEQUENCE: 36

Asp Ile Val Met Ser Gln Ser Pro Ser Ser Leu Ala Val Ser Val Gly
1               5                   10                  15

Glu Lys Val Thr Met Ser Cys Lys Ser Ser Gln Ser Leu Leu Tyr Ser
                20                  25                  30

Ser Asn Leu Lys Asn Tyr Leu Ala Trp Phe Gln Gln Lys Pro Gly Gln
            35                  40                  45

Ser Pro Lys Leu Leu Ile Tyr Trp Ala Ser Ile Arg Glu Ser Gly Val
        50                  55                  60

Pro Asp Arg Phe Thr Gly Ser Gly Ser Gly Thr Asp Phe Thr Leu Thr
65                  70                  75                  80

Ile Asn Ser Val Lys Ala Glu Asp Leu Ala Val Tyr Tyr Cys Gln Gln
                85                  90                  95

Tyr Tyr Thr Phe Pro Leu Thr Phe Gly Ala Gly Thr Lys Leu Glu Leu
                100                 105                 110

Lys

<210> SEQ ID NO 37
<211> LENGTH: 119

```
<212> TYPE: PRT
<213> ORGANISM: Artificial Sequence
<220> FEATURE:
<223> OTHER INFORMATION: SYNTHESIZED

<400> SEQUENCE: 37

Glu Val Gln Leu Val Glu Thr Gly Gly Gly Leu Val Gln Pro Lys Gly
1               5                   10                  15

Ser Leu Lys Leu Ser Cys Ala Ala Ser Gly Phe Ser Phe Asn Ile Asn
            20                  25                  30

Ala Met His Trp Val Arg Gln Ala Pro Gly Thr Gly Leu Lys Trp Val
        35                  40                  45

Ala Arg Ile Arg Ser Gly Ser Asn Asp Phe Ala Thr Tyr Tyr Ala Asp
    50                  55                  60

Ser Val Lys Asp Arg Phe Thr Ile Ser Arg Asp Asp Ser His Ser Met
65                  70                  75                  80

Leu Tyr Leu Gln Met Asn Asn Leu Lys Thr Glu Asp Thr Ala Ile Tyr
                85                  90                  95

Phe Cys Val Arg Glu Tyr Val Asn Tyr Phe Val His Trp Gly Gln Gly
            100                 105                 110

Thr Leu Val Thr Val Ser Ala
        115

<210> SEQ ID NO 38
<211> LENGTH: 12
<212> TYPE: PRT
<213> ORGANISM: Artificial Sequence
<220> FEATURE:
<223> OTHER INFORMATION: SYNTHESIZED

<400> SEQUENCE: 38

Gln Ser Leu Leu Tyr Ser Ser Asn Leu Lys Asn Tyr
1               5                   10

<210> SEQ ID NO 39
<211> LENGTH: 9
<212> TYPE: PRT
<213> ORGANISM: Artificial Sequence
<220> FEATURE:
<223> OTHER INFORMATION: SYNTHESIZED

<400> SEQUENCE: 39

Gln Gln Tyr Tyr Thr Phe Pro Leu Thr
1               5

<210> SEQ ID NO 40
<211> LENGTH: 8
<212> TYPE: PRT
<213> ORGANISM: Artificial Sequence
<220> FEATURE:
<223> OTHER INFORMATION: SYNTHESIZED

<400> SEQUENCE: 40

Gly Phe Ser Phe Asn Ile Asn Ala
1               5

<210> SEQ ID NO 41
<211> LENGTH: 10
<212> TYPE: PRT
<213> ORGANISM: Artificial Sequence
<220> FEATURE:
<223> OTHER INFORMATION: SYNTHESIZED

<400> SEQUENCE: 41
```

```
Ile Arg Ser Gly Ser Asn Asp Phe Ala Thr
1               5                   10

<210> SEQ ID NO 42
<211> LENGTH: 10
<212> TYPE: PRT
<213> ORGANISM: Artificial Sequence
<220> FEATURE:
<223> OTHER INFORMATION: SYNTHESIZED

<400> SEQUENCE: 42

Val Arg Glu Tyr Val Asn Tyr Phe Val His
1               5                   10

<210> SEQ ID NO 43
<211> LENGTH: 14
<212> TYPE: PRT
<213> ORGANISM: Artificial Sequence
<220> FEATURE:
<223> OTHER INFORMATION: SYNTHESIZED

<400> SEQUENCE: 43

Asp His Arg Asp Ala Gly Asp Leu Trp Phe Pro Gly Glu Ser
1               5                   10

<210> SEQ ID NO 44
<211> LENGTH: 11
<212> TYPE: PRT
<213> ORGANISM: Artificial Sequence
<220> FEATURE:
<223> OTHER INFORMATION: SYNTHESIZED
<220> FEATURE:
<221> NAME/KEY: MISC_FEATURE
<222> LOCATION: (2)..(2)
<223> OTHER INFORMATION: Xaa = Ser, Thr, Asn, Gln
<220> FEATURE:
<221> NAME/KEY: MISC_FEATURE
<222> LOCATION: (9)..(9)
<223> OTHER INFORMATION: Xaa = Asp, Asn

<400> SEQUENCE: 44

Gln Xaa Leu Val His Ser Asn Gly Xaa Thr Tyr
1               5                   10

<210> SEQ ID NO 45
<211> LENGTH: 9
<212> TYPE: PRT
<213> ORGANISM: Artificial Sequence
<220> FEATURE:
<223> OTHER INFORMATION: SYNTHESIZED
<220> FEATURE:
<221> NAME/KEY: MISC_FEATURE
<222> LOCATION: (3)..(3)
<223> OTHER INFORMATION: Xaa = Ser, Thr, Asn, Gln
<220> FEATURE:
<221> NAME/KEY: MISC_FEATURE
<222> LOCATION: (8)..(8)
<223> OTHER INFORMATION: Xaa = Pro, Leu

<400> SEQUENCE: 45

Ser Gln Xaa Thr His Val Pro Xaa Thr
1               5
```